(12) United States Patent
Holm et al.

(10) Patent No.: US 11,033,436 B2
(45) Date of Patent: Jun. 15, 2021

(54) TRIMMABLE CONFORMABLE WOUND DRESSING

(71) Applicant: 3M INNOVATIVE PROPERTIES COMPANY, Saint Paul, MN (US)

(72) Inventors: David R. Holm, Hudson, WI (US); Richard L. Jacobson, Stillwater, MN (US); James M. Sieracki, Plymouth, MN (US); Phong V. Ha, Hudson, WI (US); Steven B. Heinecke, New Richmond, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 115 days.

(21) Appl. No.: 16/348,212

(22) PCT Filed: Nov. 9, 2017

(86) PCT No.: PCT/US2017/060742
§ 371 (c)(1),
(2) Date: May 8, 2019

(87) PCT Pub. No.: WO2018/089563
PCT Pub. Date: May 17, 2018

(65) Prior Publication Data
US 2020/0069477 A1 Mar. 5, 2020

Related U.S. Application Data

(60) Provisional application No. 62/420,730, filed on Nov. 11, 2016.

(51) Int. Cl.
*A61F 13/00* (2006.01)
*A61F 13/02* (2006.01)

(52) U.S. Cl.
CPC ...... *A61F 13/024* (2013.01); *A61F 13/00068* (2013.01); *A61F 13/00076* (2013.01)

(58) Field of Classification Search
CPC .......... A61F 13/00072; A61F 13/00076; A61F 13/02; A61F 13/0226; A61F 13/0236;
(Continued)

(56) References Cited

U.S. PATENT DOCUMENTS 2,736,721 A 2/1956 Dexter
RE24,906 E 12/1960 Ulrich
(Continued)

FOREIGN PATENT DOCUMENTS

CN 203662982 6/2013
EP 0864311 9/1998
(Continued)

OTHER PUBLICATIONS

China National Intellectual Property Administration Search Report for CN201780076446.4, 2 pgs.
(Continued)

*Primary Examiner* — Kim M Lewis
(74) *Attorney, Agent, or Firm* — 3M Innovative Properties Company; Trisha D. Adamson

(57) ABSTRACT

Trimmable conformable wound dressings, kits containing the same and methods of using the same. The wound dressings may protect a treatment site from microbial contamination or other disturbances while a wound heals or to enable the application and maintenance of vacuum over the treatment site. The wound dressings may include first and second sections of support layer material on opposite sides of one or more intermediate sections of support layer material. The first and second sections of support layer material meet the intermediate sections of support layer material along peel tab junctions that provide peel tabs.

18 Claims, 8 Drawing Sheets

(58) Field of Classification Search
CPC .............. A61F 13/024; A61F 13/00068; A61F 13/0259; A61F 13/60; A61F 13/0246; A61F 13/0203; A61F 13/0206; A61F 13/023

See application file for complete search history.

(56) References Cited

U.S. PATENT DOCUMENTS

| | | | |
|---|---|---|---|
| 3,389,827 A | | 6/1968 | Abere |
| 3,645,835 A | | 2/1972 | Hodgson |
| 4,112,213 A | | 9/1978 | Waldman |
| 4,310,509 A | | 1/1982 | Berglund |
| 4,323,557 A | | 4/1982 | Rosso |
| 4,472,480 A | | 9/1984 | Olson |
| 4,595,001 A | | 6/1986 | Potter |
| 4,614,183 A | * | 9/1986 | McCracken .......... A61M 25/02 128/846 |
| 4,737,410 A | | 4/1988 | Kantner |
| 4,833,179 A | | 5/1989 | Young |
| 4,871,812 A | | 10/1989 | Lucast |
| 5,088,483 A | | 2/1992 | Heinecke |
| 5,160,315 A | | 11/1992 | Heinecke |
| 5,214,119 A | | 5/1993 | Leir |
| 5,266,371 A | * | 11/1993 | Sugii ................... A61F 13/023 428/131 |
| 5,531,855 A | | 7/1996 | Heinecke |
| 5,622,711 A | | 4/1997 | Chen |
| 5,633,010 A | | 5/1997 | Chen |
| 5,849,325 A | | 12/1998 | Heinecke |
| 5,908,693 A | | 6/1999 | Delgado |
| 6,083,856 A | | 7/2000 | Joseph |
| 6,171,985 B1 | | 1/2001 | Joseph |
| 6,198,016 B1 | | 3/2001 | Lucast |
| 6,368,687 B1 | | 4/2002 | Joseph |
| 6,436,432 B2 | | 8/2002 | Heinecke |
| 6,441,092 B1 | | 8/2002 | Gieselman |
| 6,518,343 B1 | | 2/2003 | Lucast |
| 6,838,589 B2 | | 1/2005 | Liedtke |
| 7,407,709 B2 | | 8/2008 | Zhou |
| 7,442,849 B2 | * | 10/2008 | Heinecke ............ A61F 13/0203 602/41 |
| 7,807,268 B2 | | 10/2010 | Zhou |
| 7,947,366 B2 | | 5/2011 | Ishiwatari |
| 8,541,481 B2 | | 9/2013 | Determan |
| 2008/0233348 A1 | | 9/2008 | Ishiwatari |
| 2013/0040073 A1 | | 2/2013 | Pett |
| 2014/0171888 A1 | | 6/2014 | Croizat |

FOREIGN PATENT DOCUMENTS

| | | | | |
|---|---|---|---|---|
| JP | 2010029242 | | 2/2010 | |
| WO | WO-9421207 A2 | * | 9/1994 | ........... A61F 13/023 |
| WO | WO 1999-27975 | | 6/1999 | |
| WO | WO 2014/409517 | | 1/2014 | |
| WO | WO 2015/102981 | | 7/2015 | |

OTHER PUBLICATIONS

International Search Report for PCT/US2017/060742 dated Jan. 19, 2018.

Satas, Handbook of Pressure Sensitive Adhesive Technology, 384-403, (1982).

* cited by examiner

TRIMMABLE CONFORMABLE WOUND DRESSING

CROSS REFERENCE TO RELATED APPLICATIONS

This application is a national stage filing under 35 U.S.C. 371 of PCT/US2017/060742, filed Nov. 9, 2017, which claims the benefit of U.S. Provisional Application No. 62/420,730, filed Nov. 11, 2016, the disclosures of which are incorporated by reference in their entirety herein.

BACKGROUND

Transparent film dressings are widely used as protective layers over wounds because they facilitate healing in a moist environment while acting as a barrier to contaminating liquids and bacteria. The films are also used as surgical drapes because of their barrier properties. The film dressings are also used as drapes in negative pressure wound therapies to enable the application and maintenance of vacuum, which has been shown to improve wound healing. Dressings and drapes fitting the above description are available under a number of trade names such as TEGADERM (3M Company, St. Paul, Minn.), BIOCLUSIVE (Johnson & Johnson Company, New Brunswick, N.J.), OP-SITE (T. J. Smith & Nephew, Hull, England), and U IPLEX (Howe Medical, Largo, Fla.).

In addition, various specifically-shaped transparent film dressings and corresponding delivery systems have been developed for applying the dressings to specific body parts or regions (e.g., a heel, the inner crease of an elbow, a shoulder, a sacral region).

The polymeric films used in those dressings and drapes generally are conformable, i.e., the films are extremely thin, flexible and supple. Typically, they are supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem.

SUMMARY

Trimmable conformable wound dressings are disclosed herein. In one or more embodiments, the dressings may be configured for application to treatment sites to protect the treatment site from microbial contamination or other disturbances while the wound heals or to enable the application and maintenance of vacuum over a wound. In one or more embodiments, the dressings described herein may be in the form of a thin, elastic polymeric film backing and a support layer removably bonded to the backing, the support layer facilitating the application of the dressing to a treatment site.

In one or more embodiments, the wound dressings described herein may include first and second sections of support layer material on opposite sides of one or more intermediate sections of support layer material. The first and second sections of support layer material meet the intermediate sections of support layer material along peel tab junctions that provide peel tabs. As result, cutting of the wound dressings may preferable result in any cropped portion of the wound dressing including one or more tabs that can be used to facilitate handling and placement of the wound dressing and, optionally, removal of the support layer after placement of the wound dressing.

In one or more embodiments, peel tab junctions defining the intermediate section extend from end to end of the wound dressing such that the wound dressings can be cut along either or both of a longitudinal axis and lateral axis (transverse to the longitudinal axis) to yield two or more cropped wound dressings that retain the support necessary to apply them to relatively smaller treatment sites.

In one or more embodiments, the wound dressings described herein may be easily applied to the body and offer simple removal of the support layer from the backing. Removal of the support layer from the backing may, in one or more embodiments, be initiated at struts located between adjacent windows. For example, the support layer can be torn or cut at more than one interior strut within a section of support layer and still be removed in one piece due to, in one or more embodiments, the use of support layer materials having increased tear strength.

In one or more embodiments, the multiple locations at which initiation of separation of the support layer from the backing can occur offers improved flexibility in trimming the dressing to a desired size without adversely affecting support of the backing during application and while offering the user multiple options for removal of the support layer after positioning of the backing layer on a wound.

In one aspect, one or more embodiments of a wound dressing as described herein includes: an elastic film backing comprising a first major surface, a second major surface opposite the first major surface, and a perimeter that includes a first end, a second end opposite the first end, first and second lateral edges, the lateral edges extending from the first end to the second end, and a longitudinal axis extending from the first end to the second end; adhesive disposed on the first major surface of the backing; and a support layer attached to the second major surface of the backing, wherein the support layer comprises a first section, a second section, and an intermediate section, wherein each of the first, second, and intermediate sections extend from the first end to the second end, wherein the first section extends from the first lateral edge of the backing to a first tab junction with the intermediate section, wherein the second section extends from the second lateral edge of the backing to a second tab junction with the intermediate section; wherein the support layer of the first tab junction comprises a first separation feature extending from the first end to the second end along the first tab junction, wherein separation of the support layer along the first separation feature forms a first section peel tab on the first section and a first intermediate tab on the intermediate section, wherein both the first section peel tab and the first intermediate tab extend from the first end to the second end of the backing; wherein the support layer of the second tab junction comprises a second separation feature extending from the first end to the second end along the second tab junction, wherein separation of the support layer along the second separation feature forms a second section peel tab on the second section and a second intermediate tab on the intermediate section, wherein both the second section peel tab and the second intermediate tab extend from the first end to the second end of the backing; wherein the first section of the support layer comprises a first frame that extends around a perimeter of the first section, and a plurality of first windows arranged along the longitudinal axis, wherein the second major surface of the backing is exposed within each first window of the plurality of first windows, and wherein each pair of adjacent first windows is separated from each other by a first strut; wherein the second section of the support layer comprises a second frame that extends around a perimeter of the second section, and a plurality of second windows arranged along the longitudinal axis, wherein the second major surface of the backing is exposed within each second window of the plurality of second windows, and wherein each pair of adjacent second windows is separated from each other by a second strut; wherein the intermediate section of the support layer comprises an intermediate frame that extends around a perimeter of the intermediate section, and a plurality of intermediate windows arranged along the longitudinal axis, wherein the second major surface of the backing is exposed within each intermediate window of the plurality of intermediate windows, and wherein each pair of adjacent intermediate windows is separated from each other by an intermediate strut.

In one or more embodiments, at least a portion of the support layer forming the first section peel tab and the first intermediate tab is not attached to the second major surface of the backing, and wherein at least a portion of the support layer forming the second section peel tab and the second intermediate tab is not attached to the second major surface of the backing.

In one or more embodiments, the first and/or second section peel tabs exhibit a total hand value greater than a total hand value of the support layer of their respective first or second section.

In a second aspect, one or more embodiments of a kit are described herein, the kit comprising a sealed package containing one or more wound dressings as described herein; packing material, wherein the packing material optionally comprises open cell foam; and a port with tubing.

In a third aspect, one or more embodiments of a method of deploying a wound dressing as described herein may include: removing the release liner from the adhesive; attaching the backing over a treatment site using the adhesive; and removing the one or more of the first section of the support layer, the second section of the support layer, and the intermediate section of the support layer after attaching the backing over the treatment site.

One or more embodiments of the methods described herein may include cutting the wound dressing along a longitudinal cut line extending from the first end to the second end of the wound dressing to reduce the size of the wound dressing before removing the release liner and/or cutting the wound dressing along a transverse cut line extending in a direction transverse to the longitudinal axis of the wound dressing to reduce the size of the wound dressing before removing the release liner.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a tab can be interpreted to mean "one or more" tabs.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the dressings and methods described herein. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any illustrative embodiments are described in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used or positioned in use.

Conformable wound dressings as described herein are highly-conformable and have an adhesive disposed on one side. Thus, in the absence of a suitable support structure to support the dressings during placement at the treatment site, the dressings may be susceptible to folding back on themselves. The wound dressings described herein provide structural features that not only support the dressing during application to a treatment site; they also enable the use of such conformable dressings to treat relatively large, highly-contoured treatment sites such as, e.g., knees, etc.

In one or more embodiments, the support layer is adapted so that the wound dressing can be easily cut along either or both of a longitudinal axis and lateral axis (transverse to the longitudinal axis) into two or more smaller wound dressings, each smaller wound dressing preferably including all of the necessary support features to facilitate its application to a smaller contoured treatment site.

Figure 1:
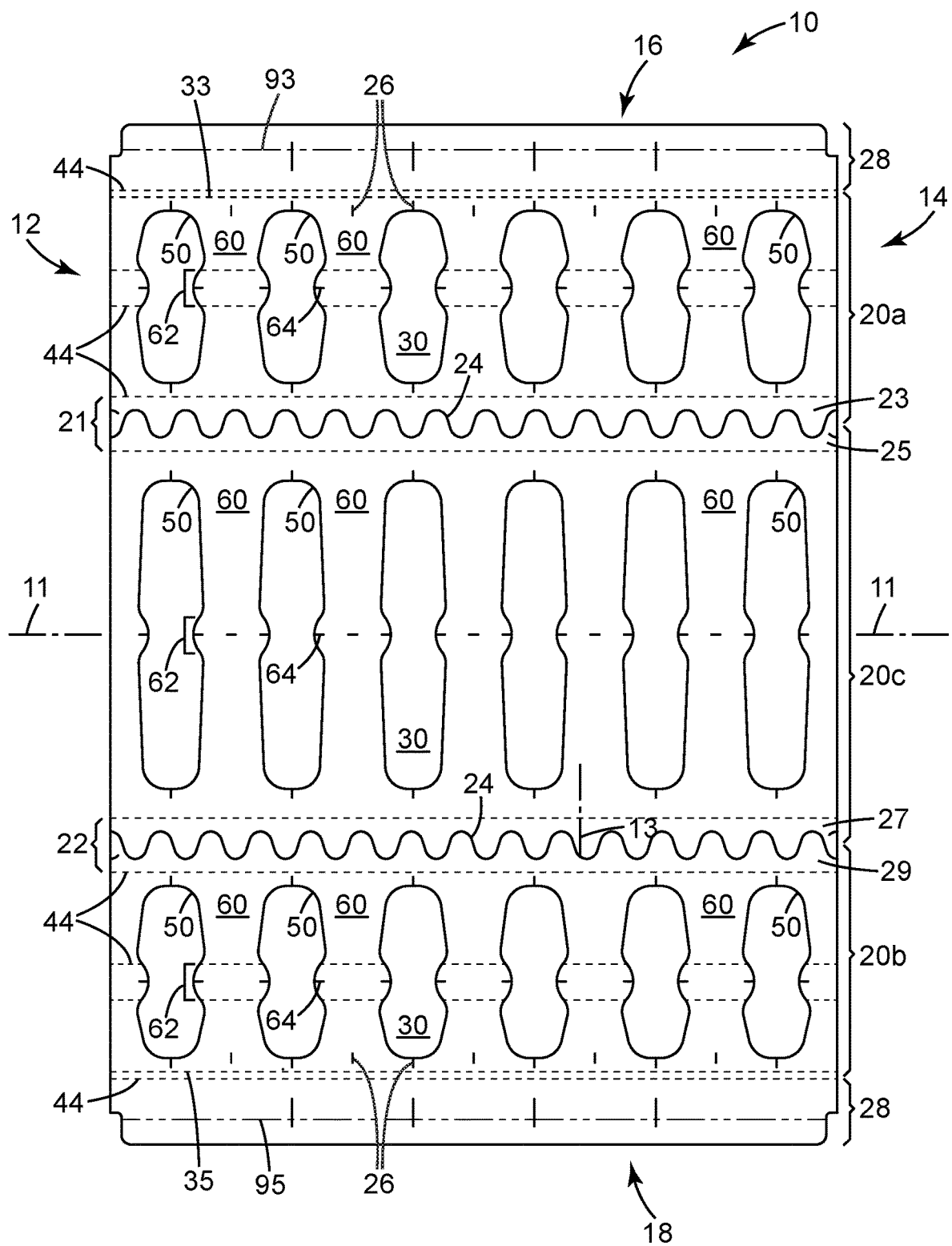
FIG. 1 is a plan view of one illustrative embodiment of a wound dressing as described herein.
Figure 2:
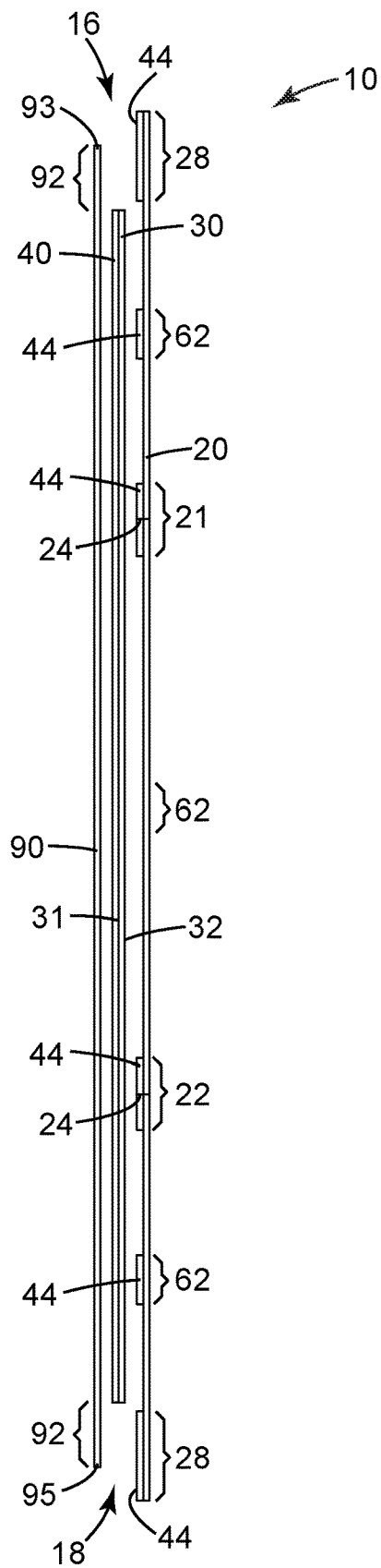
FIG. 2 is an exploded side view of the wound dressing of FIG. 1.

FIGS. 1 and 2 depict one embodiment of a wound dressing designated in its entirety by the reference numeral 10. The wound dressing 10 comprises an elastic film backing 30, a support layer 20, and a release liner 90, where the backing 30 is located between the support layer 20 and the release liner 90.

In one or more embodiments, the wound dressing 10 includes a first end 12, a second end 14 opposite the first end 12, and a longitudinal axis 11 extending between the first end 12 and the second end 14. In one or more embodiments, the longitudinal axis 11 can be coincident with a central axis of the wound dressing 10 where, e.g., the central axis is equidistant from the first and second lateral edges described below). The wound dressing 10 also includes a first lateral edge 16 and a second lateral edge 18, with both of the lateral edges 16 and 18 extending from the first end 12 to the second end 14 of the wound dressing 10. Together, the first and second ends 12 and 14 and the first and second lateral edges 16 and 18 of the wound dressing 10 define a perimeter of the wound dressing 10.

The backing 30 has a perimeter that includes, in one or more embodiments, a first end aligned with the first end 12 of the wound dressing 10 and a second end that is also aligned with the second end 14 of the wound dressing 10. The perimeter of the backing 30 also includes a first lateral edge 33 positioned along the first lateral edge 16 of the wound dressing 10, as well as a second lateral edge 35 positioned along the second lateral edge 18 of the wound dressing 10. Both of the lateral edges 33 and 35 of the backing 30 extend from the first end 12 to the second end 14.

The backing 30 of the wound dressing 10 is the portion of the wound dressing 10 that is applied to a treatment site (not shown) and is left on the treatment site for a period of time. The support layer 20 of the wound dressing 10 facilitates the proper application of the backing 30 to the treatment site. Although removal of the support layer 20 is not required, typically, the support layer is removed after the backing 30 is applied to the wound. The elastic film backing 30 includes a first major surface 31 and a second major surface 32 opposite the first major surface. Although the depicted embodiment of wound dressing 10 is generally rectangular in shape, one or more embodiments of the wound dressings described herein can be formed in a variety of shapes including, for example, a trapezoid, a square, etc. and may, in one or more embodiments, include rounded corners for each of the various shapes.

Referring to FIG. 2, the backing 30 may include a first major surface 31 (sometimes referred to as the "bottom face" or "patient-facing surface" of the backing 30) and a second major surface 32 (sometimes referred to as the "top face" of the backing 30).

Adhesive 40 may, in one or more embodiments, be disposed (e.g., as a coated layer) on the first major surface 31 of the backing 30. The adhesive 40 is typically in the form of a pressure-sensitive adhesive (PSA). Adhesive 40 may be applied as a continuous coating covering substantially the entire first major surface 31 of the backing 30. In one or more alternative embodiments, the adhesive 40 may be coated discontinuously (e.g., in various types of porous patterns, not shown) on a portion of the first major surface 31.

One or more embodiments of the backing of wound dressings as described herein may also include a low adhesion coating (low adhesion backsize or LAB) on the second major surface 32 of the backing 30. A description of one potentially suitable low adhesion coating for use with the backing of one or more embodiments of a wound dressing as described herein can be found in Example 1 of U.S. Pat. No. 5,531,855. The low adhesion coating is, in one or more embodiments, compatible with a heat seal bond described herein. The low adhesion coating may, in one or more embodiments, reduce dressing changes due to unwanted dressing removal when tapes or devices are placed on the backing 30 of wound dressing 10 and then removed. In addition, the low adhesion coating may reduce surface friction between the backing 30 on linen or other fabrics, thereby offering additional protection against the accidental removal of the backing 30 during use.

In one or more embodiments, the support layer 20 of the wound dressing 10 is attached to the second major surface 32 of the backing 30 such that the backing 30 is located between the adhesive 40 and the support layer 20. The support layer 20 may, in one or more embodiments, be removably bonded onto the second major surface 32 of the backing 30, as described herein. In one or more embodiments, the support layer 20 may be mounted (i.e., removably bonded) onto the second major surface 32 of the backing 30 (over low adhesion coating, if present) with a heat seal bond. In such embodiments, the heat seal bond between the support layer 20 and the backing 30 is stronger than the bond between the adhesive 40 and the release liner 90 so that the backing 30 remains attached to the support layer 20 when release liner 90 is removed from the wound dressing 10. Once the release liner 90 and wound dressing 10 are separated, only the support layer 20 and any other components (e.g. and absorbent pad, etc.), if present, remain attached to the backing 30.

The support layer 20 may, in one or more embodiments, be described as forming a first section 20a, a second section 20b, and an intermediate section 20c on the backing 30. Each of the first, second, and intermediate sections 20a, 20b, and 20c extend from the first end 12 to the second end 14 of the dressing 10. In one or more embodiments, the first section 20a extends along the first lateral edge 16 of the wound dressing 10 to a first tab junction 21 with the intermediate section 20c. The second section 20b extends along the second lateral edge 18 of the wound dressing 10 to a second tab junction 22 with the intermediate section 20c. As a result, the intermediate section 20c of the support layer 20 is located between the first and second sections 20a and 20b of the support layer 20. Although the depicted illustrative embodiments of wound dressing 10 includes only one intermediate section 20c, one or more alternative embodiments of wound dressings as described herein may include two or more intermediate sections, each separated from adjacent intermediate sections by a tab junction similar to tab junctions 21 and 22.

In one or more embodiments, the wound dressing 10 also includes a pair of handle tabs 28 positioned along the first and second lateral edges 16 and 18 of the wound dressing 10. The handle tab 28 attached to the first section 20a of the support layer 20 may, in one or more embodiments, be described as located along and extending away from the first lateral edge 33 of the backing 30 from the first end to the second end of the backing 30. The handle tab 28 attached to the second section 20b of the support layer 20 may, in one or more embodiments, be described as located along and extending away from the second lateral edge 35 of the backing 30 from the first end to the second end of the backing 30.

In one or more embodiments, one or both of the handle tabs 28 may be integral with the section (20a or 20b) of the support layer 20 from which they extend. In one or more alternative embodiments, one or both of the handle tabs 28 may be provided by a separate and discrete article attached to the support layer 20 along a lateral edge of the wound dressing 10.

In one or more embodiments, the handle tabs 28 may be stiffer than the support layer 20 that supports the bulk of the backing 30 in the first section 20a and/or second section 20b. In the depicted illustrative embodiment, each of the handle tabs 28 includes a bond-block layer 44 attached to the support layer 20 to increase the stiffness of the handle tab relative to the remainder of the support layer 20 of each of the first sections 20a and second section 20b. In one or more embodiments, the bond-block layer 44 may be the same as that used for the bond block layers described herein, but that is not required. In one or more embodiments, the increased stiffness of the handle tabs may be characterized in terms of total hand (stiffness), with the handle tabs exhibiting a total hand (stiffness) value greater than a total hand (stiffness) value of the support layer of the section to which the handle tab is attached.

One or more embodiments of wound dressings as described herein may include a release liner 90 detachably attached to the exposed surface of adhesive 40 on the first major surface 31 of the backing 30. The release liner 90 covers the adhesive 40 until the operator is ready to apply the wound dressing 10 to a treatment surface. The release liner 90 may, in one or more embodiments, be a single piece or multiple piece release liner, and may be part of or laminated to a package (not shown) containing the wound dressing, or merely enclosed along with the wound dressing 10 within the package.

The release liner 90 may, in one or more embodiments, form at least one release liner tab 92 that extends beyond the first and second lateral edges 33 and 35 of the backing 30, where the first and second lateral edges 33 and 35 of the backing 30 are positioned inward from the first and second lateral edges 16 and 18 of the wound dressing 10.

In one or more embodiments, the release liner tab 92 can overlap a handle tab 28 that also extends past the first end second lateral edges 33 and 35 of the backing 30. As used herein, a first piece can be said to "overlap" or "overlie" a second piece if it covers a portion of either the second piece, or a portion of some third piece that is covered along its opposite side by the second piece. In other words, one piece can "overlap" or "overlie" another piece even though separated by a third piece.

In the depicted illustrative embodiment, the release liner 90 has a first edge 93 that is not aligned with the first lateral edge 16 of the wound dressing 10 as defined by the handle tab 28 and a second edge 95 that is not aligned with the second lateral edge 18 of the wound dressing 10 as defined by the handle tab 28. Those non-aligned edges may improve the ability of a user to grasp the liner 90 and/or the handle tabs 28.

The first tab junction 21 between the intermediate section 20c and the first section 20a and the second tab junction 22 between the intermediate section 20c and the second section 20b both include a separation feature 24 that extends from the first end 12 to the second end 14 of the wound dressing 10. The separation features 24 are provided to facilitate the formation of peel tabs on the side of each of the first and second sections 20a and 20b that is adjacent the intermediate section 20c. In particular, the separation feature 24 in the first tab junction 21 forms the edges of peel tabs 23 and 25, with peel tab 23 formed on the first section 20a and peel tab 25 formed on the intermediate section 20c. Separation feature 24 in the second tab junction 22 forms the edges of peel tabs 27 and 29, with peel tab 27 formed on the intermediate section 20c and peel tab 29 formed on the second section 20b.

The separation features 24 may, in one or more embodiments, take a variety of different forms to promote separation of the support layer 20 along the separation feature 24 such as, e.g., a line/area of weakness (e.g., a crease, a fold, a thinned portion (e.g., thinned by embossing), a perforation, a plurality of perforations, a slit, a plurality of slits, etc. In one or more embodiments, the separation layer 20 may be completely separated along the separation features 24 by, e.g., a continuous slit or cut extending from the first end 12 to the second end 14 of the dressing 10. In one or more alternative embodiments, the support layer 20 may remain connected across the separation features 24, with flexing or other manipulation of the wound dressing 10 and/or the support layer 20 along at least a portion of the separation feature 24 being used to finish complete separation of the support layer 20 across the separation feature 24.

The support layer 20 may, in one or more embodiments, not be attached to the backing 30 along the first tab junction 21 and/or the second tab junction 22 to further promote separation of the support layer 20 along the separation features 24 in one or both of the junctions 21 and/or 22. In one or more embodiments of the wound dressing as described herein, a bond-block zone may be provided to prevent bonding between the support layer 20 and the backing 30 in the area of the first tab junction 21 and/or second tab junction 22. FIG. 2 depicts one illustrative embodiment of a bond-block in the form of a bond-block layer 44 that may be located between the support layer 20 and the backing 30. In one or more embodiments, the bond-block layer 44 may be applied (e.g., via a lamination process) to the support layer 20 and/or the backing 30. One non-limiting illustrative example of a potentially suitable bond-block layer 44 is 3M™ MICROPORE™ Tape (available from 3M Company, St. Paul, Minn.). In one or more embodiments, the separation features 24 may be formed through/in the bond-block layer 44 as well as the support layer 20 as illustrated in, e.g., FIGS. 2 and 3.

To facilitate handling of the peel tabs formed along the tab junctions 21 and 22, one or more embodiments of the wound dressings as described herein may include peel tabs that are stiffer than the support layer 20 that supports the bulk of the backing 30 in the first section 20a, second section 20b, or intermediate section 20c to which the peel tab is attached. In the depicted illustrative embodiment, the tab junctions 21 and 22 each include a layer of material 44 attached to the support layer 20 to serve as a bond block. In one or more embodiments, the bond block material 44 may also increase the stiffness of the peel tab relative to the remainder of the support layer 20 of the corresponding first sections 20a, second section 20b, or intermediate section 20c. In one or more embodiments, the material that increases the stiffness of the peel tabs may be the same as that used for the bond blocks, but that is not required (e.g., a separate layer of material could be attached over the surface of the support layer 20 facing away from the backing 30 to increase the stiffness of the support layer in the tab junctions). In one or more embodiments, the increased stiffness of the peel tabs may be characterized in terms of total hand (stiffness), with the peel tabs exhibiting a total hand (stiffness) value greater than a total hand (stiffness) value of the support layer of the section to which the peel tab is attached.

In one or more embodiments of the wound dressings as described herein, the first section 20a of the support layer 20 may be described as forming a first frame that extends around a perimeter of the first section 20a. The first frame formed by the first section 20a may, in one or more embodiments, be described as providing continuous, unbroken support for the lateral edge 33 and the edges of the backing 30 located along the first and second ends 12 and 14 of the dressing 10. In one or more embodiments, the first frame may be described as including a first lateral edge member that extends along the first lateral edge 16 of the wound dressing 10 from the first end 12 to the second end 14. The first frame further includes a first tab junction member extending along the first tab junction 21 from the first end 12 to the second end 14 of the wound dressing 10. The first frame also includes a first end member that extends along the first end 12 of the wound dressing 10 from the first lateral edge 16 of the wound dressing 10 to the first tab junction member extending along the first tab junction 21. Finally, the first frame includes a second end member that extends along the second end 14 of the wound dressing 10 from the first lateral edge of the wound dressing 10 to the first tab junction member extending along the first tab junction 21.

The first section 20a of the support layer 20 also includes, in one or more embodiments, a plurality of first windows 50 arranged along the longitudinal axis 11 of the wound dressing 10. The second major surface 32 of the backing 30 is exposed within each first window 50 in the first section 20a of the support layer 20. Each pair of adjacent first windows 50 in the first section 20a is separated from each other by a first strut 60 that extends across the first frame from the first lateral edge member located along the first lateral edge 16 of the wound dressing 10 to the first tab junction member that extends along the first tab junction 21.

The windows 50 in the first section 20a of the support layer 20 may, in one or more embodiments, be cut (e.g., controlled depth die cut) from a support layer blank (not shown) to form a support layer 20 having windows 50 that expose a portion of the top surface of the backing 30. The window portion of the support layer 20 may, in one or more embodiments, be removed during manufacturing of the wound dressing 10 or by the consumer at the time of using the wound dressing 10.

The windows 50 formed in the support layer 20 provide, after their removal, increased visibility in order for the operator to view the treatment site as the wound dressing 10 is being positioned over the treatment site and, subsequently applied to the site. In addition, the windows 50 may also provide, after their removal, increased flexibility when conforming the backing 30 to the treatment site during application.

The struts 60 separating adjacent pairs of windows 50 in the first section 20a of the support layer 20 may, in one or more embodiments, include a tear location 62 located along each of the struts 60. In one or more embodiments, the tear location 62 is positioned between the first lateral edge member (located along the first lateral edge 16 of the dressing 10) and the first tab junction member (located along the first tab junction 21). The support layer 20 forming the tear location 62 of each of the struts 60 is, in one or more embodiments, configured to preferentially separate at the tear location 62.

In one or more embodiments, the tear location 62 of one or more of the struts 60 in the first section 20a may include one or more features configured to promote tearing of the strut 60. In one or more embodiments, the tear location of each strut 60 may include one or more of a notch 64 formed in an edge of the support layer 20 at the tear location 62 of each first strut 60, a slit or other line of weakness extending between each pair of adjacent first windows 50 at the tear location 62 of each strut 60, etc.

In one or more embodiments of the wound dressings as described herein, the second section 20b of the support layer 20 may be described as forming a second frame that extends around a perimeter of the second section 20b. The second frame formed by the second section 20b may, in one or more embodiments, be described as providing continuous, unbroken support for the second lateral edge 35 and the edges of the backing 30 located along the first and second ends 12 and 14 of the dressing 10. The second frame includes a second lateral edge member that extends along the second lateral edge 18 of the wound dressing 10 from the first end 12 to the second end 14. The second frame further includes a second junction member extending along the second tab junction 22 from the first end 12 to the second end 14 of the wound dressing 10. The second frame also includes a first end member that extends along the first end 12 of the wound dressing 10 from the second lateral edge 18 of the wound dressing 10 to the second junction member extending along the second tab junction 22. Finally, the second frame includes a second end member that extends along the second end 14 of the wound dressing 10 from the second lateral edge 18 of the wound dressing 10 to the second junction member extending along the second tab junction 22.

The second section 20b of the support layer 20 also includes, in one or more embodiments, a plurality of second windows 50 arranged along the longitudinal axis 11 of the wound dressing 10. The second major surface 32 of the backing 30 is exposed within each second window 50 in the second section 20b of the support layer 20. Each pair of adjacent second windows 50 in the second section 20b is separated from each other by a second strut 60 that extends across the second frame from the second lateral edge member located along the second lateral edge 18 of the wound dressing 10 to the second junction member that extends along the second tab junction 22.

The windows 50 in the second section 20b of the support layer 20 may, in one or more embodiments, be cut (e.g., controlled depth die cut) from a support layer blank (not shown) to form a support layer 20 having windows 50 that expose a portion of the top surface of the backing 30. The window portion of the support layer 20 may, in one or more embodiments, be removed during manufacturing of the wound dressing 10 or by the consumer at the time of using the wound dressing 10.

The windows 50 formed in the support layer 20 provide, after their removal, increased visibility in order for the operator to view the treatment site as the wound dressing 10 is being positioned over the treatment site and, subsequently applied to the site. In addition, the windows 50 may also provide, after their removal, increased flexibility when conforming the backing 30 to the treatment site during application.

The struts 60 separating adjacent pairs of windows 50 in the second section 20b of the support layer 20 may, in one or more embodiments, include a tear location 62 located along each of the struts 60. In one or more embodiments, the tear location 62 is positioned between the second lateral edge member (located along the second lateral edge 18 of the dressing 10) and the second junction member (located along the second tab junction 22). The support layer forming the tear location 62 of each of the struts 60 is, in one or more embodiments, configured to preferentially separate at the tear location 62.

In one or more embodiments, the tear location 62 of one or more of the struts 60 in the second section 20b may include one or more features configured to promote tearing of the strut 60. In one or more embodiments, the tear location of each strut 60 may include one or more of a notch 64 formed in an edge of the support layer 20 at the tear location 62 of each first strut 60, a slit or other line of weakness extending between each pair of adjacent first windows 50 at the tear location 62 of each strut 60, etc.

In one or more embodiments of the wound dressings as described herein, the intermediate section 20c of the support layer 20 may be described as forming an intermediate frame that extends around a perimeter of the intermediate section 20c. The intermediate frame formed by intermediate section 20c may, in one or more embodiments, be described as providing continuous, unbroken support for the edges of the backing 30 located along the first and second ends 12 and 14 of the dressing 10, as well as the entire length of the backing along the tab junctions formed between the intermediate section 20c and any neighboring support layer sections such as, e.g., tab junctions 21 and 22. The intermediate frame includes a first intermediate junction member extending along the first tab junction 21 from the first end 12 to the second end 14 of the dressing 10. The intermediate frame further includes a second intermediate junction member extending along the second tab junction 22 of the wound dressing 10 from the first end 12 to the second end 14 of the wound dressing 10. The intermediate frame also includes a first intermediate end member that extends along the first end 12 of the wound dressing 10 from the first tab junction 21 to the second tab junction 22 of the wound dressing 10. Finally, the intermediate frame includes a second intermediate end member that extends along the second end 14 of the wound dressing 10 from the first tab junction 21 to the second tab junction 22 of the wound dressing 10.

The intermediate section 20c of the support layer 20 also includes, in one or more embodiments, a plurality of intermediate windows 50 arranged along the longitudinal axis 11 of the wound dressing 10. The second major surface 32 of the backing 30 is exposed within each intermediate window 50 in the intermediate section 20c of the support layer 20. Each pair of adjacent intermediate windows 50 in the intermediate section 20c is separated from each other by an intermediate strut 60 that extends across the intermediate frame from the first intermediate junction member extending along the first tab junction 21 to the second intermediate junction member that extends along the second tab junction 22.

The windows 50 in the intermediate section 20c of the support layer 20 may, in one or more embodiments, be cut (e.g., controlled depth die cut) from a support layer blank (not shown) to form a support layer 20 having windows 50 that expose a portion of the top surface of the backing 30. The window portion of the support layer 20 may, in one or more embodiments, be removed during manufacturing of the wound dressing 10 or by the consumer at the time of using the wound dressing 10.

The windows 50 formed in the support layer 20 provide, after their removal, increased visibility in order for the operator to view the treatment site as the wound dressing 10 is being positioned over the treatment site and, subsequently applied to the site. In addition, the windows 50 may also provide, after their removal, increased flexibility when conforming the backing 30 to the treatment site during application.

The struts 60 separating adjacent pairs of windows 50 in the intermediate section 20c of the support layer 20 may, in one or more embodiments, include a tear location 62 located along each of the struts 60. In one or more embodiments, the tear location 62 is positioned between the second lateral edge member (located along the second lateral edge 18 of the dressing 10) and the second junction member (located along the second tab junction 22). The support layer forming the tear location 62 of each of the struts 60 is, in one or more embodiments, configured to preferentially separate at the tear location 62.

In one or more embodiments, the tear location 62 of one or more of the struts 60 in the second section 20b may include one or more features configured to promote tearing of the strut 60. In one or more embodiments, the tear location of each strut 60 may include one or more of a notch 64 formed in an edge of the support layer 20 at the tear location 62 of each first strut 60, a slit or other line of weakness extending between each pair of adjacent first windows 50 at the tear location 62 of each strut 60, etc.

In one or more embodiments, the support layer 20 may not be attached to the backing 30 at the tear location 62 of any of the struts 60 in the first section 20a, second section 20b, and/or intermediate section 20c such that separation of the support layer 20 from the backing 30 and subsequent tearing of the support layer 20 forming the strut 60 may be more readily achieved. Detachment of the support layer 20 from the backing 20 in the tear locations may, in one or more embodiments, be combined with any one or more of other features configured to promote tearing of the strut (e.g., a notch, a slit, or other line of weakness) as described herein.

In one or more embodiments, a wound dressing as described herein may include a bond-block zone to prevent bonding between the support layer 20 and the backing 30 in the area of the tear location. FIG. 2 depicts one illustrative embodiment of a tear location bond-block in the form of a bond-block layer 44 that may be located between the support layer 20 and the backing 30 in the area occupied by the tear location 62. In one or more embodiments, the bond-block layer 44 may be applied (e.g., via a lamination process) to the support layer 20 and/or the backing 30. One non-limiting illustrative example of a potentially suitable bond-block layer 44 is 3M™ MICROPORE™ Tape (available from 3M Company, St. Paul, Minn.). In one or more embodiments in which the bond-block layer 44 is in the form of physical article (such as, e.g., a tape, etc.), any features configured to promote tearing of the strut 60 (e.g., a notch, a slit, or other line of weakness, etc.) may be formed through/in the bond-block layer 44 as well as the support layer 20.

Figure 3:
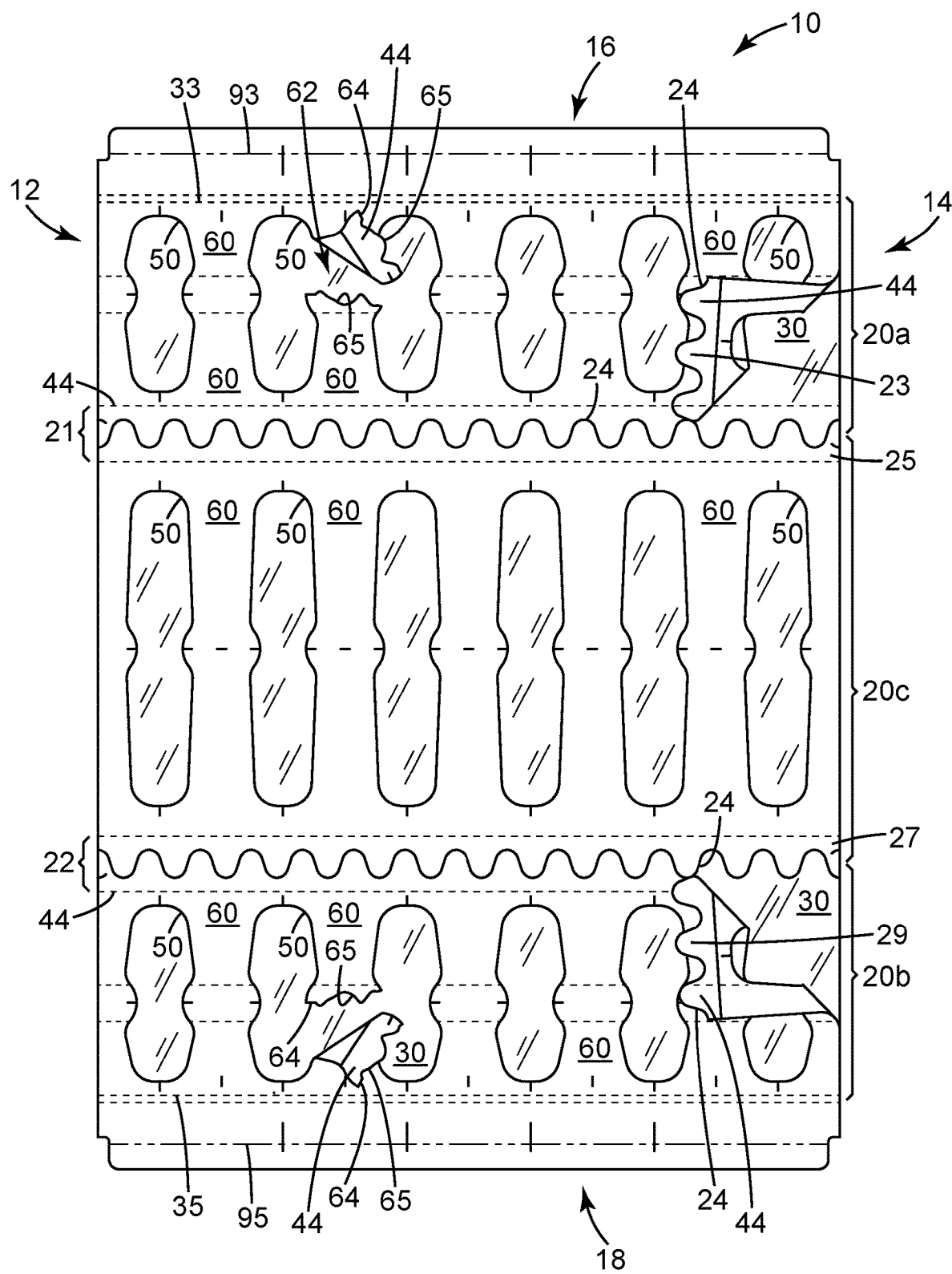
FIG. 3 is a plan view depicting illustrative methods of removing the support layer from the backing for the illustrative embodiment of the wound dressing of FIGS. 1 and 2.

FIG. 3 depicts the dressing 10 of FIGS. 1 and 2 during initiation of removal of the support layer 20 in both the first section 20a and the second section 20b. In particular, a strut 60 located between an adjacent pair of windows 50 in each of the first section 20*a* and the second section 20*b* is depicted after being torn and partially removed from the backing 30. The tearing of the struts 60 may, in the depicted embodiment, be initiated at notches 64 which then propagate into tear lines 65 that extend across the width of each of the struts 60.

In addition, removal of the first section 20*a* and the second section 20*b* of the support layer 20 are also depicted as being initiated along the peel tabs formed by separation features 24 located along first tab junction 21 between the first section 20*a* and the intermediate section 20*c* as well as the second tab junction 22 between the second section 20*b* and the intermediate section 20*c*.

In particular, peel tab 23 is depicted as being used to separate the support layer of the first section 20*a* from the backing 30, while peel tab 29 is depicted as being used to separate the support layer 20 of the second section 20*b* from the backing 30. The increased stiffness provided by, in the depicted illustrative embodiment, bond-block layer 44 attached to the support layer 20 along each of the tab junctions 21 and 22 may improve the ability of the user to remove the support layer 20 using the peel tabs.

Another optional feature of one or more embodiments of wound dressings as described herein includes slits 26 formed through the support layer 20 of the first section 20*a* between the windows 50 and the first lateral edge 33 of the backing 30. The slits 26 may, in one or more embodiments, assist with removal of the first section 20*a* of the support layer 20 from the backing 30 after attached of the backing 30 over a treatment site. In one or more embodiments, the slits 26 are positioned such that they do not intersect or lie over the first lateral edge 33 of the backing 30. Although not required, in one or more embodiments, the slits 26 may be aligned with each other along the first lateral edge 33 of the backing 30 such that they are equidistant from the lateral edge 33 of the backing 30. One or more of the slits 26 may, in one or more embodiments, be located between the struts 60 separating the windows 50. One or more of the slits 26 may, in one or more embodiments, intersect a perimeter of a window 50. Further, one or more of the slits 26 may, in one or more embodiments, be oriented transverse to the longitudinal axis 11 of the wound dressing 10.

Slits 26 may also, in one or more embodiments, be provided in the second section 20*b* between the windows 50 and the second lateral edge 35 of the backing 30. The slits 26 may, in one or more embodiments, assist with removal of the second section 20*b* of the support layer 20 from the backing 30 after attached of the backing 30 over a treatment site. In one or more embodiments, the slits 26 are positioned such that they do not intersect or lie over the second lateral edge 35 of the backing 30. Although not required, in one or more embodiments, the slits 26 may be aligned with each other along the second lateral edge 35 of the backing 30 such that they are equidistant from the lateral edge 35 of the backing 30. One or more of the slits 26 may, in one or more embodiments, be located between the struts 60 separating the windows 50. One or more of the slits 26 may, in one or more embodiments, intersect a perimeter of a window 50. Further, one or more of the slits 26 may, in one or more embodiments, be oriented transverse to the longitudinal axis 11 of the wound dressing 10.

As discussed herein the increased tear strength of the support layer material may facilitate removal of entire sections (e.g., first section 20*a*, second section 20*b*, and/or intermediate sections 20*c*) even though that removal may be initiated at as few as one location in each of the sections.

Figure 4:
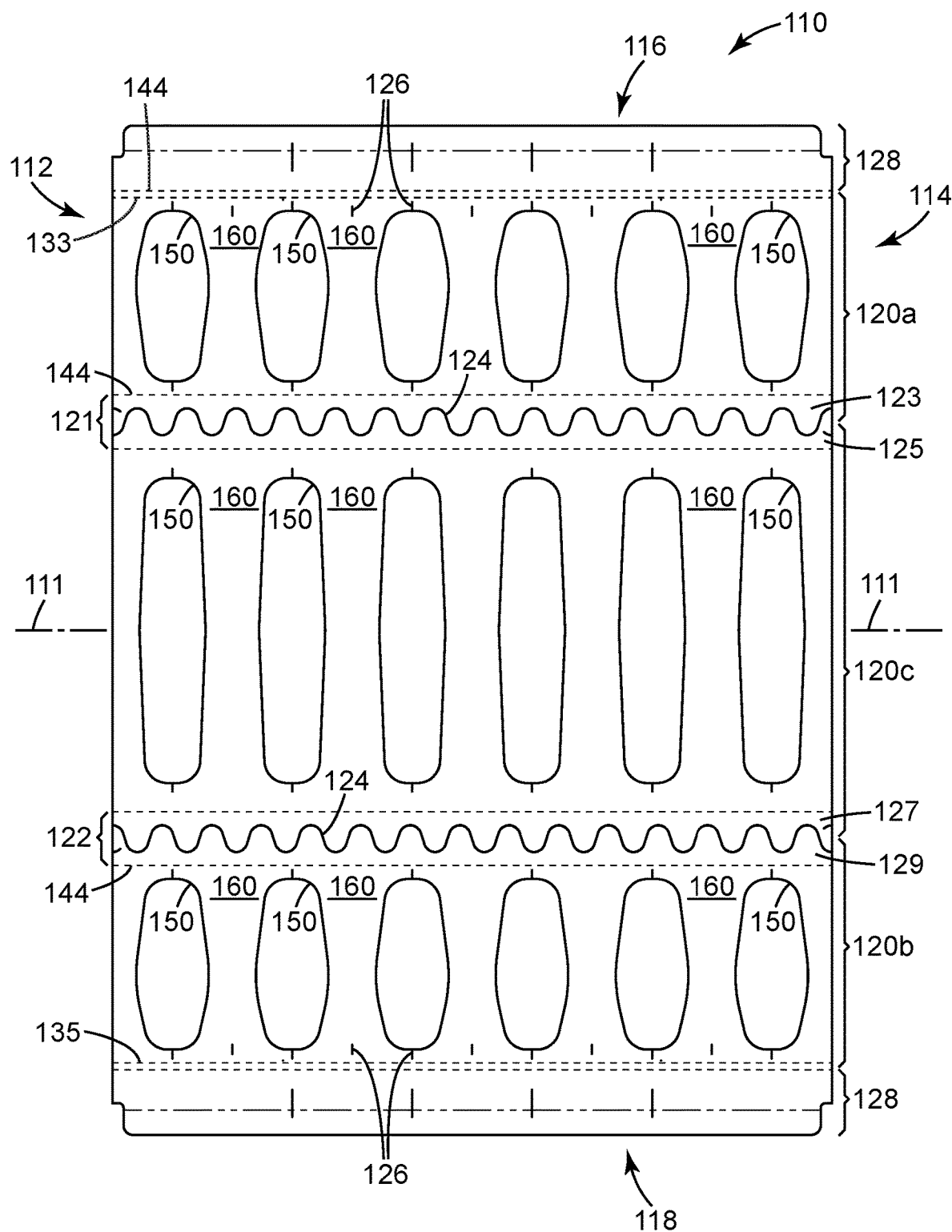
FIG. 4 depicts one alternative illustrative embodiment of a wound dressing as described herein.
Figure 5:
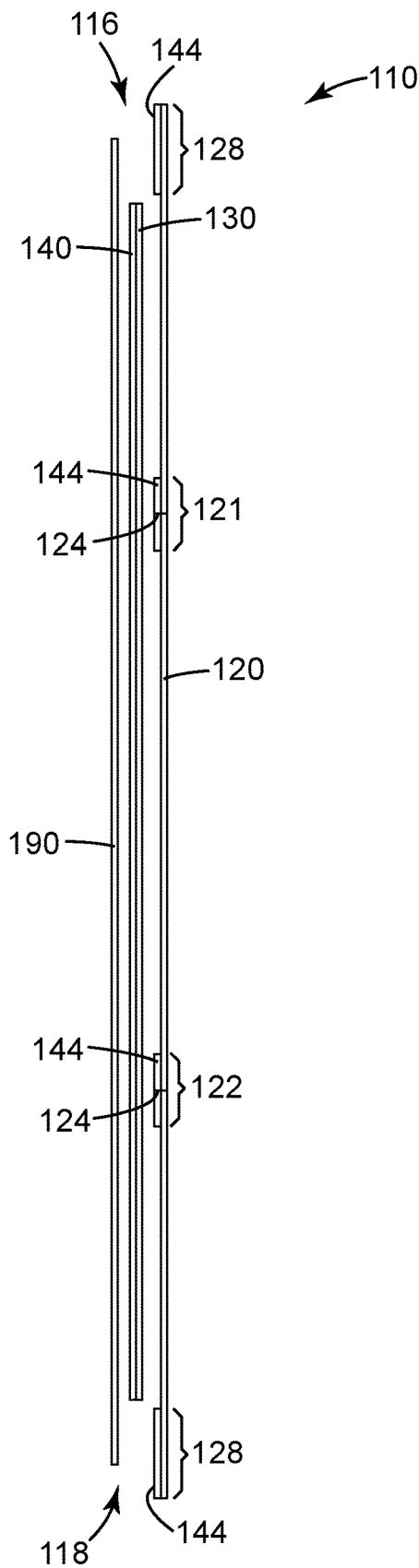
FIG. 5 is an exploded side view of the wound dressing of FIG. 4.
Figure 6:
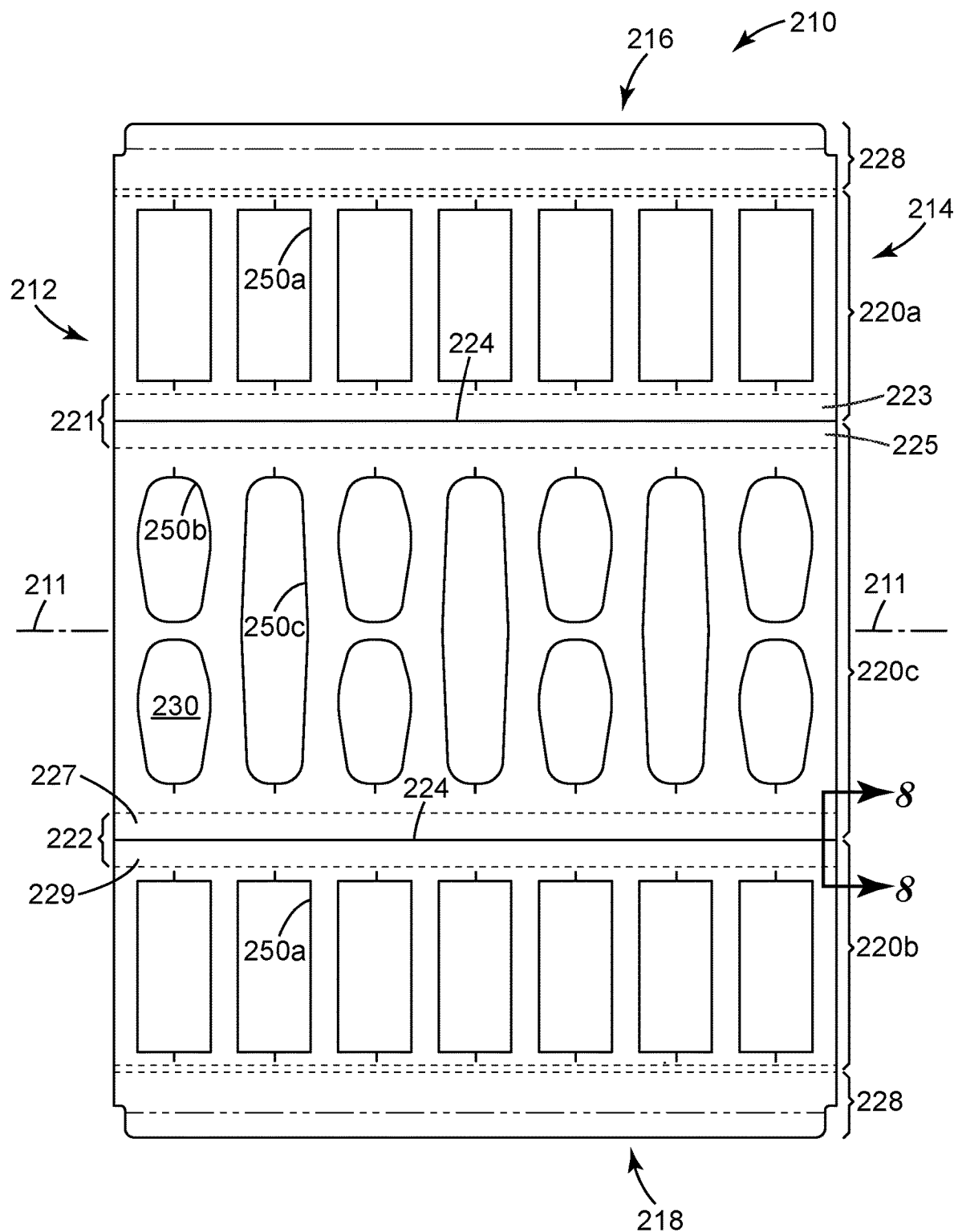
FIG. 6 is a plan view of another alternative illustrative embodiment of a wound dressing as described herein.

Another illustrative embodiment of a wound dressing as described herein is depicted in FIGS. 4 and 5. The depicted illustrative embodiment of wound dressing 110 is similar to the illustrative embodiment of wound dressing 10. The wound dressing 110 comprises an elastic film backing 130, a support layer 120, and a release liner 190, where the backing 130 is located between the support layer 120 and the release line 190.

In one or more embodiments, the wound dressing 110 includes a first end 112, a second end 114 opposite the first end 112, and a longitudinal axis 111 extending between the first end 112 and the second end 114 of the dressing 110. The wound dressing 110 also includes a first lateral edge 116 and a second lateral edge 118, with both of the lateral edges 116 and 118 extending from the first end 112 to the second end 114 of the wound dressing 110. Together, the first and second ends 112 and 114 and the first and second lateral edges 116 and 118 of the wound dressing 110 define a perimeter of the wound dressing 110.

Adhesive 140 may, in one or more embodiments, be disposed (e.g., as a coated layer) on the backing 130 as described in connection with dressing 10, along with an LAB coating. Further, a release liner 190 may also be provided to protect adhesive 140 as discussed above in connection with dressing 10.

In one or more embodiments, the support layer 120 of the wound dressing 110 is attached to the backing 130 as described above in connection with dressing 10.

The support layer 120 of dressing 110 may, in one or more embodiments, be described as forming a first section 120*a*, a second section 120*b*, and an intermediate section 120*c* on the backing 130 as described above in connection with dressing 10. Similarly, a first tab junction 121 between the intermediate section 120*c* and the first section 120*a* as well as the second junction 122 between the intermediate section 120*c* and the second section 120*b* along with a separation feature 124 that extends from the first end 112 to the second end 114 of the wound dressing 110 may also be provided as described above in connection with dressing 10. The separation feature 124 in first tab junction 121 defines the edges of peel tabs 123 and 125 in the first section 120*a* and the intermediate section 120*c* as discussed above in connection with wound dressing 10. Similarly, separation feature 124 in second tab junction 122 defines the edges of peel tabs 127 and 129 in the intermediate section 120*c* and the second section 120*b* as discussed above in connection with wound dressing 10.

Stiffness of the peel tabs formed in the tab junctions 121 and 122 as well as in handle tabs 128 formed along the lateral edges 116 and 118 of the dressing 110 may be increased using, in the depicted embodiment, material 144 as discussed above in connection with dressing 10.

In one or more embodiments of the wound dressing 110, the first section 120*a* of the support layer 120 may be described as forming a first frame that extends around the first section 120*a*, the second section 120*b* of the support layer 120 may be described as forming a second frame that extends around the second section 120*b*, and the intermediate section 120*c* may be described as forming an intermediate frame that extends around the intermediate section 120*c* as described above in connection with dressing 10.

Further, each of the first section 120*a*, second section 120*b*, and intermediate section 120*c* also includes, as described above in connection with dressing 10, a set of windows 150 formed in the support layer 120. Each pair of adjacent windows 150 is separated from each other by a strut 160 that extends across the respective frame as described above in connection with dressing 10.

One difference between the wound dressing 10 of FIGS. 1-3 and the wound dressing 110 of FIGS. 4 and 5 is that the struts 160 separating adjacent pairs of windows 150 in the wound dressing 110 do not include a tear location. As a result, separation of the different sections of the support layer 120 of the dressing 110 may, in one or more embodiments, be initiated along the peel tabs 123, 125, 127, and 129 formed along separation features 124 in each of the first tab junction 121 and the second tab junction 122.

The illustrative embodiment of wound dressing 110 also includes sets of slits 126 formed through the support layer 120 arranged inwardly along each of the first and second lateral edges 133 and 135 of the backing 130 (similar to slits 26 described in connection with dressing 10 above).

Another illustrative embodiment of a wound dressing as described herein is depicted in FIGS. 6, 7, 8A and 8B. The depicted illustrative embodiment of wound dressing 210 is, in many respects similar to the illustrative embodiments of wound dressing 10 and 110. The wound dressing 210 includes an elastic film backing 230, a support layer 220, and a release liner 290, where the backing 230 is located between the support layer 220 and the release liner 290.

In one or more embodiments, the wound dressing 210 includes a first end 212, a second end 214, and a longitudinal axis 211 extending between the first end 212 and the second end 214 of the dressing 210. The wound dressing 210 also includes a first lateral edge 216 and a second lateral edge 218, with both of the lateral edges 216 and 218 extending from the first end 212 to the second end 214 of the wound dressing 210. Together, the first and second ends 212 and 214 and the first and second lateral edges 216 and 218 of the wound dressing 210 define a perimeter of the wound dressing 210.

Adhesive may, in one or more embodiments, be disposed (e.g., as a coated layer) on the backing 230 as described in connection with dressing 10, along with an LAB coating. Further, a release liner 290 may also be provided to protect the adhesive on the backing 230 as discussed above in connection with dressing 10.

In one or more embodiments, the support layer 220 of the wound dressing 210 is attached to the backing 230 as described above in connection with dressing 10.

The support layer 220 of dressing 210 may, in one or more embodiments, be described as forming a first section 220a, a second section 220b, and an intermediate section 220c on the backing 230 as described above in connection with dressing 10. Similarly, a first tab junction 221 between the intermediate section 220c and the first section 220a as well as a second tab junction 222 between the intermediate section 220c and the second section 220b are provided along with a separation feature 224 as described above in connection with dressing 10. The separation feature 224 in first tab junction 221 defines the edges of peel tabs 223 and 225 in the first section 220a and the intermediate section 220c as discussed above in connection with wound dressing 10. Similarly, separation feature 224 in second tab junction 222 defines the edges of peel tabs 227 and 229 in the intermediate section 220c and the second section 220b as discussed above in connection with wound dressing 10.

One difference is that separation features 224 in dressing 210 are formed as straight lines rather than the undulating lines of separation features 24 and 124 in the embodiments discussed above to illustrate that the separation features used in tab junctions of wound dressings as described herein may take any suitable shape or form.

One difference between the wound dressings 10 and 110 of FIGS. 1-5 is that the windows provided in the dressing 210 have different shapes and arrangements to illustrate that the windows provided in wound dressings as described herein may have any suitable shapes and/or arrangements.

In the depicted illustrative embodiment, the windows 250a formed in the first sections 220a and the second section 220b have a different shape from the windows 250b and 250c formed in the support layer 220 of the intermediate section 220c. Further, although the windows 250a in the first section 220a and second section of 220b have the same size, shape and arrangement, this is not required, i.e., the windows provided in the first sections may be different in size, shape, and/or arrangement from the windows in the second sections of wound dressings as described herein.

Figure 8A:
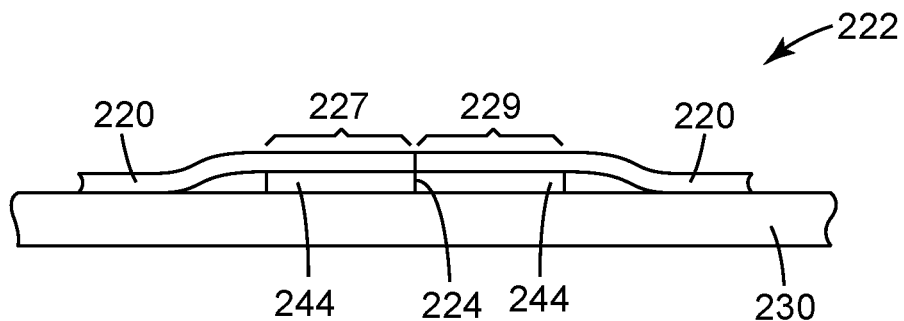
FIG. 8A is an enlarged cross-sectional view of the wound dressing of FIG. 6 taken along line 8-8 in FIG. 6.
Figure 8B:
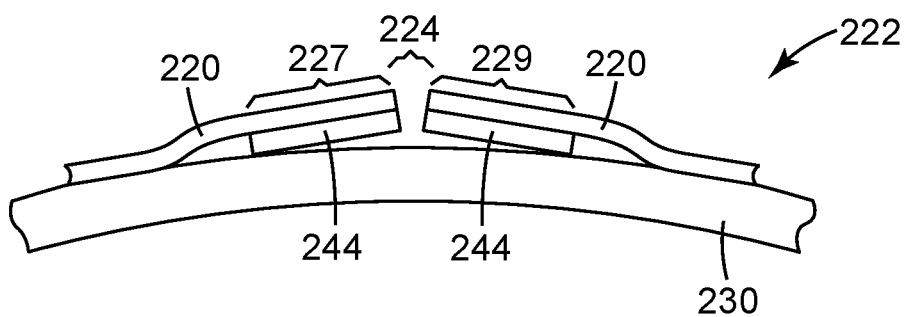
FIG. 8B is a view of the wound dressing of FIG. 8A after separation of the support layer.

The enlarged cross-sectional views of the illustrative embodiment of the wound dressing 210 as seen in FIGS. 8A and 8B depict the peel tabs 227 and 229 and their separation or detachment from the backing 230. In particular, layer 244 may, in one or more embodiments, prevent attachment of the support layer 220 to the backing 230 and increase stiffness of the peel tabs 227 and 229 as discussed herein. Flexing or manipulation of the dressing 210 as seen in, e.g., FIG. 8B may facilitate grasping of the peel tabs 227 and 229 as they separate from each other across separation feature 224.

Figure 7:
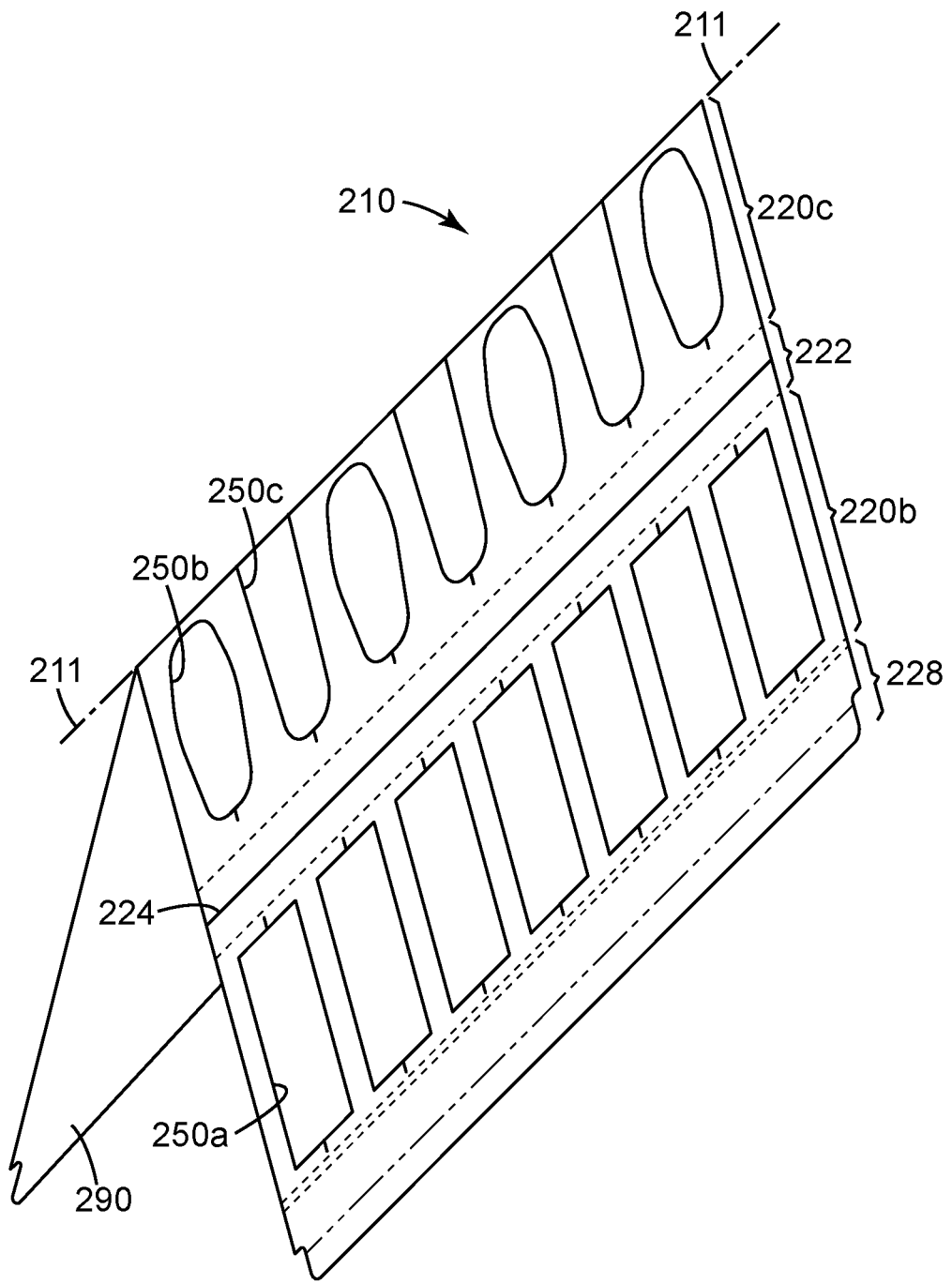
FIG. 7 is a perspective view of the wound dressing of FIG. 7 after folding along the longitudinal axis 211.

Turning to FIG. 7, in one or more embodiments, the dressings 210 as described herein may be folded along a fold line that extends between the first and second tab junctions 221 and 222. Although dressing 210 is folded along a fold line that is coincident with the longitudinal axis 211, this arrangement is not required. Further, in one or more alternate embodiments, the wound dressings described herein may be folded at any location between the first and second tab junctions. In still other variations, the wound dressings described herein may be folded along fold lines that are located in one or both of the first and second sections (e.g., first and second sections 220a and 220b). It may be preferred that fold lines in the wound dressings as described herein do not cross either or both of any tab junctions (e.g., tab junctions 221 and 222) and/or handle tabs (e.g., handle tabs 228).

As discussed herein, the windows provided in the support layer of wound dressings as described herein may take any suitable size, shape and/or arrangement. In one or more embodiments, the windows in any of the sections of the support layer of wound dressings as described herein may have a maximum width (measured along the longitudinal axis) of 1 centimeter or more. The windows may, in one or more embodiments, have a maximum width of 4 centimeters or less. In one or more embodiments, the windows may have a maximum length (measured along a lateral axis extending transverse to the longitudinal axis) of 2 centimeters or more. In one or more embodiments, the windows may have a maximum length of 10 centimeters or less, optionally 20 cm or less. In one or more embodiments, the longest dimension of the windows may be perpendicular to the longitudinal axis.

The wound dressings described herein may, in one or more embodiments, be characterized in terms of a ratio of maximum window width to minimum strut width for the pairs of adjacent windows and the struts located between the pairs of adjacent windows. In one or more embodiments of the wound dressings described herein, a maximum window width to minimum strut width ratio may be, e.g., 0.25 or more, optionally 0.5 or more, optionally 1 or more, or optionally 2 or more. At an upper end, the ratio of maximum window width to minimum strut width ratio may, in one or more embodiments, be, e.g., 4 or less, optionally 3.5 or less, optionally 3 or less, or optionally 2.5 or less.

Figure 9:
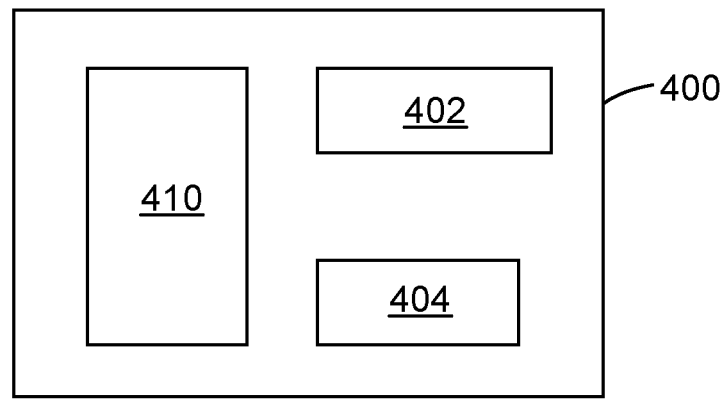
FIG. 9 is a schematic diagram of on illustrative kit including one or more wound dressings as described herein.

The wound dressings as described herein may be provided in a kit along with other components. Referring to FIG. 9, one or more embodiments of a kit 400 containing one or more wound dressings 410 as described herein may also include packing material 402 and a port with tubing 404 configured for connection to a vacuum source if the one or more wound dressings 410 are to be used to deliver negative wound pressure therapy. Potentially suitable packing materials may include, e.g., an open cell foam or any other material capable of remaining open to the passage of fluid after being located over a treatment site beneath the backing of the wound dressings described herein. One example of a potentially suitable open cell foam is a reticulated, open-celled polyurethane foam having a pore size range of 400-600 micron. An example of this type of foam is the GRANUFOAM™ foam used in the negative pressure wound therapy kits provided by Acelity (San Antonio, Tex.).

Wound dressings as described herein can be used to cover treatment sites on a patient that have a variety of different sizes and, as a result, the wound dressings described herein may be provided in a variety of sizes. In one or more embodiments, wound dressings as described herein may be provided in sizes as measured along the longitudinal axis from first end to second that range from 12 centimeters or more, optionally 15 centimeters or more, optionally 20 centimeters or more, or optionally 25 centimeters or more. As measured along a transverse axis extending between the first and second lateral edges of the wound dressings described herein, one or more embodiments of the wound dressings may have a transverse dimension of 20 centimeters or more, optionally 25 centimeters or more, optionally 30 centimeters or more, or optionally 35 centimeters or more.

Because the treatment sites come in a variety of different sizes, the user may, in one or more embodiments, cut the wound dressings described herein to tailor the wound dressing to the size of a treatment site. The arrangement of support layer sections along with handle tabs and tab junctions of wound dressings as described herein may provide the user with improved options for cutting the wound dressings to a selected size without sacrificing the support needed to effectively apply the flexile backings of the wound dressings over a treatment site. The cutting typically is performed before removing a release liner (if present) from the wound dressing.

With reference to the illustrative embodiment of wound dressing 10 as depicted in FIG. 1, one or more embodiments of methods of using the wound dressings as described herein may include cutting the wound dressing 10 along a cut line extending from the first end 12 to the second end 14 of the wound dressing 10. In one or more embodiments, the cut line may be located in the intermediate section 20c between the first tab junction 21 and the second tab junction 22. In one or more embodiments, the cut line may be coincident with and/or parallel to the longitudinal axis 11 of the dressing 10, but that is not required. Further, the cut line may follow a fold line (see, e.g., illustrative embodiment of wound dressing 210 in FIG. 7), but that is not required.

Cutting the dressing 10 along a cut line that extends through the intermediate section 20c from the first end 12 to the second end 14 of the dressing 10 may be advantageous because the portions of the dressing 10 on either side of the cut line will include at least two tabs to facilitate handling of that portion of the wound dressing 10. For example, the portion of the dressing 10 containing the first section 20a and a portion of the intermediate section 20c would include peel tabs 23 and 25 along with handle tab 28 extending from first section 20a. Similarly, the portion of the dressing 10 containing the second section 20b and a portion of the intermediate section 20c would include peel tabs 27 and 29 along with handle tab 28 extending from the second section 20b. As discussed herein, providing handle tabs and/or peel tabs with increased stiffness may further improve handling of the cut portions of the dressing 10.

In addition to, or in place of, cuts extending through the intermediate section, one or more embodiments of methods of using the wound dressings described herein may include cutting the dressings along one or more lines extending from the first end 12 to the second end 14 of the dressing 10 through either or both of the first section 20a and second section 20b. Even in those methods, at least one edge of the portion of the first section 20a/second section 20b separated from the wound dressing 10 would include a handle tab 28 to facilitate handling of that portion of the wound dressing 10.

Still further, one or more embodiments of methods of using the wound dressings described herein may involve cutting the wound dressing along one or more transverse cut lines, where a transverse cut line would extend between the first and second lateral edges 16 and 18 of the wound dressing. The wound dressings may, in one or more embodiments, be cut along a transverse cut line before and/or after cutting the wound dressing along a longitudinal cut line. In one or more embodiments, the transverse cut line may pass through one or both of the first tab junction 21 and the second tab junction 22 of the wound dressing 10.

It may be preferred that cutting of the wound dressings as described herein leave any portion of the dressing that is to be applied to a treatment site with at least one handle tab 28 and/or tab junction 21 or 22 intact to provide one or more tabs that facilitate handling of the cut portion during application of the cut portion of the wound dressing to a treatment site and, optionally, to facilitate removal of the support layer if so desired.

Backing Materials

Suitable backings used in one or more embodiments of the wound dressings described herein may include polymer films. In one or more embodiments, the backing materials are translucent or transparent polymeric elastic films. Most preferably, the backing is a high moisture vapor permeable film backings. U.S. Pat. No. 3,645,835, the disclosure of which is hereby incorporated by reference, describes methods of making such films and methods for testing their permeability.

In one or more embodiments, the film (including any adhesive coated thereon) transmits moisture vapor at a rate equal to or greater than human skin. Preferably, the adhesive coated film transmits moisture vapor at a rate of at least 300 g/m2/24 hrs/37° C./100-10% RH, more preferably at least 700 g/m2/24 hrs/37° C./100-10% RH, and most preferably at least 2000 g/m2/24 hrs/37° C./100-10% RH using the inverted cup method.

The backing may also, in one or more embodiments, be conformable to anatomical surfaces. As such, when the backing is applied to an anatomical surface, it conforms to the surface even when the surface is moved. The backing may also conformable to animal anatomical joints. When the joint is flexed and then returned to its unflexed position, the backing stretches to accommodate the flexion of the joint, but is resilient enough to continue to conform to the joint when the joint is returned to its unflexed condition. In one or more embodiments, the backing has an ultimate elongation of greater than 200%, and, in one or more alternative embodiments, the backing has an ultimate elongation of greater than 400%.

A description of this characteristic of backings that may be used in one or more embodiments of the wound dressings described herein can be found in issued U.S. Pat. Nos. 5,088,483 and 5,160,315. Particularly preferred backings may be, e.g., elastomeric polyurethane, co-polyester, or polyether block amide films. These films combine the desirable properties of resiliency, high moisture vapor permeability, and transparency found in preferred backings.

Support Layer Materials

The support layer material used to supply the support layer 20 and sections thereof is preferably more rigid than the backing 30 to prevent the backing from wrinkling during application. The support layer material can be heat-sealable to the backing 30, with or without the low adhesion coating described above. The support layers used in one or more embodiments of the wound dressings described herein may be a polyethylene/vinyl acetate copolymer coated polyester film, polyvinylacetate coated polyester film, or polyethylene film. In one or more embodiments in which a coated polyester film is used for a support layer, the polyester film may have a thickness of between 15 and 55 microns. In one or more embodiments in which polyvinylacetate coated polyester film material is used as a support layer, the coated film may have a thickness of between 20 and 100 microns thick.

The support layers used in one or more embodiments of wound dressings as described herein may also include one or more layers of materials such as non-wovens, polymer films, or papers at distinct locations within the support layer delivery system attached to the aforementioned polymer films. One example of a suitable support layer material is that used in the manufacture of the 90024 3M™ TEGADERM™ Hydrocolloid Thin Dressing as discussed in Example 1.

In those embodiments in which the support layer includes one or more struts with tear locations, the support layer may, in at least the portions of the support layer that form the tear locations, an average trouser tear strength of 200 grams or more, optionally 300 grams or more (when tested as described herein).

In one or more embodiments, the support layer used in wound dressings as described herein that is not located in a peel tab or a handle tab may be constructed to exhibit an ultimate elongation of greater than 10%, and preferably greater than 20%.

In one or more embodiments, a support layer attached to the backing of one or more embodiments of wound dressings as described herein has a total hand value of 20 grams or more, optionally 40 grams or more, or optionally 60 grams or more (when tested as described herein). In one or more embodiments, the support layer may have a total hand value of 600 grams or less, optionally 500 grams or less, or optionally 400 grams or less.

As discussed herein, the peel tabs and/or the handle tabs may, in one or more embodiments, have a total hand value greater than the support layer to which they are attached/to which they extend from. In one or more embodiments, the peel tabs of wound dressings as described herein may have a total hand value (when tested as described herein) of 250 grams or more, optionally 400 grams or more.

Adhesive

Any reasonably skin compatible pressure sensitive adhesive can be used for adhesive 40. Examples of potentially suitable skin contact pressure sensitive adhesives (PSAs) include rubber based adhesives (e.g., tackified natural rubbers, synthetic rubbers, and styrene block copolymers), acrylics (e.g., polymerized (meth)acrylates), poly(alpha-olefins), polyurethanes, and silicones. Amine containing polymers can also be used which have amine groups in the backbone, pendant thereof, or combinations thereof. A suitable example includes a poly(ethyleneimine).

Useful adhesives can be any of those that are compatible with skin and useful for wound dressings, such as those disclosed in U.S. Pat. No. Re. 24,906 (Ulrich), U.S. Pat. No. 5,849,325 (Heinecke et al.), and U.S. Pat. No. 4,871,812 (Lucast et. al.) (water-based and solvent-based adhesives); U.S. Pat. No. 4,833,179 (Young et al.) (hot-melt adhesives); U.S. Pat. No. 5,908,693 (Delgado et al.) (microsphere adhesives); U.S. Pat. Nos. 6,171,985 and 6,083,856 (both to Joseph et al.) (low trauma fibrous adhesives); and, U.S. Pat. No. 6,198,016 (Lucast et al.), U.S. Pat. No. 6,518,343 (Lucast et al.), and U.S. Pat. No. 6,441,092 (Gieselman) (wet-skin adhesives). Inclusion of medicaments or antimicrobial agents in the adhesive is also contemplated, as described in U.S. Pat. No. 4,310,509 (Berglund) and U.S. Pat. No. 4,323,557 (Rosso).

Silicone and acrylic based pressure sensitive adhesives are most commonly utilized for adhering to the skin.

Silicone PSAs typically include two major components, a polymer or gum, and a tackifying resin. The polymer is typically a high molecular weight polydimethylsiloxane or polydimethyl-diphenylsiloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is endcapped with trimethylsiloxy groups (OSiMe3) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.). In some embodiments, the silicone adhesive may be characterized as gentle to skin such as described in U.S. Pat. No. 8,541,481, US2013/0040073, U.S. Pat. Nos. 7,407,709 and 7,807,268. Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350.

Acrylic adhesive typically comprise a copolymer of at least one $C_4$-$C_{12}$ alkyl (meth)acrylate such as isooctyl acrylate or 2-ethylehexylacrylate and at least one high Tg (e.g. polar) comonomer such as (meth)acrylamide, N-vinyl pyrrolidone, poly(ethylene oxide)acrylate, and mixture thereof. In typical embodiments, the acrylic adhesive comprises at least 90 wt.-% $C_4$-$C_{12}$ alkyl (meth)acrylate(s). Suitable examples include a 90:10 isooctyl acrylate:acrylic acid copolymer, a 70:15:15 isooctyl acrylate:ethylene oxide acrylate:acrylic acid terpolymer, and a 25:69:6 2-ethylhexylacrylate:butyl acrylate:acrylic acid terpolymer. Another acrylic adhesive composition includes a 97:3 isooctyl acrylate: acrylamide copolymer 65:15:20 2-ethylhexylacrylate:acrylic acid:copolymer blended with a nonreactive polyalkylene oxide copolymer under the trade designation PLURONIC. Additional useful adhesives are described in U.S. Pat. Nos. 3,389,827, 4,112,213, 4,310,509, and 4,323,557.

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348 (now U.S. Pat. No. 7,947,366), the disclosures of which are incorporated herein by reference. Each of the securing or skin-contact adhesive can optionally be applied in a discontinuous manner.

Absorbent Pad Materials

Absorbent pads that may be delivered using the backings of one or more embodiments of the wound dressings described herein can be manufactured of any of a variety of materials including, but not limited to, foams, gels, hydrocolloids, wovens or nonwovens. Absorbent pads may be useful for containing a number of substances, including antimicrobial agents, drugs for transdermal drug delivery, chemical indicators to monitor hormones or other substances in a patient, etc.

In one or more embodiments, an absorbent pad may be in the form of an island pad providing an absorbent matrix includes the normal adhesives which are applied to the skin, or the hydrocolloid compositions described in U.S. Pat. Nos. 5,622,711 and 5,633,010. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (x-link CMC) (e.g. Ac-Di-Sol®; FMC Corp., Philadelphia, Pa.), a synthetic hydrocolloid, such as cross-linked polyacrylic acid (PAA) (e.g., CARBOPOL® No. 974P; B.F. Goodrich, Brecksville, Ohio), or a combination thereof. Preferably, the hydrocolloid absorbent component comprises from about 5 percent to about 60 percent by weight of the adhesive composition. When preparing anti adhesive composition for use in a wound dressing the hydrocolloid absorbent preferably comprises from about 20 percent to about 40 percent by weight of the composition.

Release Liner Materials

Release liners used in one or more embodiments of the wound dressings described herein may be made of Kraft papers, polyethylene, polypropylene, polyester or composites of any of these materials. The liners are preferably coated with release agents such as fluorochemicals or silicones. For example, U.S. Pat. No. 4,472,480 describes low surface energy perfluorochemical liners. The liners used in one or more embodiments of the wound dressings described herein may be papers, polyolefin films, or polyester films coated with silicone release materials. Examples of commercially available silicone coated release papers are silicone release papers available from Loparex (Cary, N.C.) or silicone coated poly films available from Huhtamaki (Forchheim, Germany)

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. Considerations pertinent to the selection of a silicone release liner can be found in Chapter 18 of the Handbook of Pressure Sensitive Adhesive Technology, Van Nostrand-Reinhold, 1982, pp. 384-403. U.S. Pat. No. 4,472,480 also describes considerations pertinent to the selection of a perfluoropolyether release liner.

Liners are available from a variety of manufacturers in a wide variety of proprietary formulations. Those skilled in the art will normally test those liners in simulated use conditions against an adhesive of choice to arrive at a product with the desired release characteristics.

ILLUSTRATIVE EMBODIMENTS

The following non-limiting illustrative embodiments of the wound dressings, kits including wound dressings, and methods may be provided.

Embodiment 1. A wound dressing comprising: an elastic film backing comprising a first major surface, a second major surface opposite the first major surface, and a perimeter that includes a first end, a second end opposite the first end, first and second lateral edges, the lateral edges extending from the first end to the second end, and a longitudinal axis extending from the first end to the second end; adhesive disposed on the first major surface of the backing; and a support layer attached to the second major surface of the backing, wherein the support layer comprises a first section, a second section, and an intermediate section, wherein each of the first, second, and intermediate sections extend from the first end to the second end, wherein the first section extends from the first lateral edge of the backing to a first tab junction with the intermediate section, wherein the second section extends from the second lateral edge of the backing to a second tab junction with the intermediate section; wherein the support layer of the first tab junction comprises a first separation feature extending from the first end to the second end along the first tab junction, wherein separation of the support layer along the first separation feature forms a first section peel tab on the first section and a first intermediate tab on the intermediate section, wherein both the first section peel tab and the first intermediate tab extend from the first end to the second end of the backing; wherein the support layer of the second tab junction comprises a second separation feature extending from the first end to the second end along the second tab junction, wherein separation of the support layer along the second separation feature forms a second section peel tab on the second section and a second intermediate tab on the intermediate section, wherein both the second section peel tab and the second intermediate tab extend from the first end to the second end of the backing; wherein the first section of the support layer comprises a first frame that extends around a perimeter of the first section, and a plurality of first windows arranged along the longitudinal axis, wherein the second major surface of the backing is exposed within each first window of the plurality of first windows, and wherein each pair of adjacent first windows is separated from each other by a first strut; wherein the second section of the support layer comprises a second frame that extends around a perimeter of the second section, and a plurality of second windows arranged along the longitudinal axis, wherein the second major surface of the backing is exposed within each second window of the plurality of second windows, and wherein each pair of adjacent second windows is separated from each other by a second strut; wherein the intermediate section of the support layer comprises an intermediate frame that extends around a perimeter of the intermediate section, and a plurality of intermediate windows arranged along the longitudinal axis, wherein the second major surface of the backing is exposed within each intermediate window of the plurality of intermediate windows, and wherein each pair of adjacent intermediate windows is separated from each other by an intermediate strut.

Embodiment 2. A wound dressing according to embodiment 1, wherein at least a portion of the support layer forming the first section peel tab and the first intermediate tab is not attached to the second major surface of the backing, and wherein at least a portion of the support layer forming the second section peel tab and the second intermediate tab is not attached to the second major surface of the backing.

Embodiment 3. A wound dressing according to any one of embodiments 1 to 2, wherein the first section peel tab exhibits a total hand value greater than a total hand value of the support layer of the first section.

Embodiment 4. A wound dressing according to any one of embodiments 1 to 3, wherein the second section peel tab exhibits a total hand value greater than a total hand value of the support layer of the second section.

Embodiment 5. A wound dressing according to any one of embodiments 1 to 4, wherein the first separation feature comprises a slit formed through the support layer, and wherein the second separation comprises a slit formed through the support layer.

Embodiment 6. A wound dressing according to any one of embodiments 1 to 5, wherein a first handle tab is located along and extends away from the first lateral edge of the backing from the first end to the second end of the backing.

Embodiment 7. A wound dressing according to embodiment 6, wherein the first handle tab exhibits a total hand value greater than a total hand value of the support layer of the first section.

Embodiment 8. A wound dressing according to any one of embodiments 1 to 7, wherein a second handle tab is located along and extends away from the second lateral edge of the backing from the first end to the second end of the backing.

Embodiment 9. A wound dressing according to embodiment 8, wherein the second handle tab exhibits a total hand value greater than a total hand value of the support layer of the second section.

Embodiment 10. A wound dressing according to any one of embodiments 1 to 9, wherein the support layer forming the first frame, the second frame, and the intermediate frame exhibits a trouser tear strength of 200 grams or more or, optionally, 300 grams or more.

Embodiment 11. A wound dressing according to any one of embodiments 1 to 10, wherein the support layer forming the first frame, the second frame, and the intermediate frame exhibits a total hand value 600 grams or less, optionally 500 grams or less, or optionally, 400 grams or less.

Embodiment 12. A wound dressing according to any one of embodiments 1 to 11, wherein the support layer forming the first frame, the second frame, and the intermediate frame exhibits a total hand value of 20 grams or more, optionally 40 grams or more, optionally 60 grams or more, or optionally 80 grams or more.

Embodiment 13. A wound dressing according to any one of embodiments 1 to 12, wherein the first tab junction and the second tab junction exhibit a total hand value of 150 grams or more, optionally 200 grams or more, optionally 300 grams or more, or optionally 400 grams or more.

Embodiment 14. A wound dressing according to any one of embodiments 1 to 13, wherein the support layer forming the first frame, the second frame, and the intermediate frame exhibits ultimate elongation of 10% or more, optionally 20% or more.

Embodiment 15. A wound dressing according to any one of embodiments 1 to 14, wherein the first section of the support layer comprises a plurality of first slits formed through the support layer, wherein the plurality of first slits are located between the first windows and the first lateral edge of the backing.

Embodiment 16. A wound dressing according to embodiment 15, wherein the plurality of first slits are aligned along the first lateral edge of the backing.

Embodiment 17. A wound dressing according to any one of embodiments 15 to 16, wherein the plurality of first slits do not intersect the first lateral edge of the backing.

Embodiment 18. A wound dressing according to any one of embodiments 15 to 17, wherein one or more first slits of the plurality of first slits are located between the first struts separating the first windows.

Embodiment 19. A wound dressing according to any one of embodiments 15 to 18, wherein at least one slit of the plurality of first slits intersects a perimeter of a first window.

Embodiment 20. A wound dressing according to any one of embodiments 15 to 19, wherein one or more first slits of the plurality of first slits is oriented transverse to the longitudinal axis.

Embodiment 21. A wound dressing according to any one of embodiments 1 to 20, wherein the second section of the support layer comprises a plurality of second slits formed through the support layer, wherein the plurality of second slits are located between the second windows and the second lateral edge of the backing.

Embodiment 22. A wound dressing according to embodiment 21, wherein the plurality of second slits are aligned along the second lateral edge of the backing.

Embodiment 23. A wound dressing according to any one of embodiments 21 to 22, wherein the plurality of second slits do not intersect the second lateral edge of the backing.

Embodiment 24. A wound dressing according to any one of embodiments 21 to 23, wherein one or more second slits of the plurality of second slits are located between the second struts separating the second windows.

Embodiment 25. A wound dressing according to any one of embodiments 21 to 24, wherein at least one second slit of the plurality of second slits intersects a perimeter of a second window.

Embodiment 26. A wound dressing according to any one of embodiments 21 to 25, wherein one or more second slits of the plurality of second slits is oriented transverse to the longitudinal axis.

Embodiment 27. A wound dressing according to any one of embodiments 1 to 26, wherein the wound dressing comprises a tear location located along at least one first strut, wherein the tear location is positioned between a pair of adjacent first windows, wherein the support layer forming the first strut is configured to preferentially separate at the tear location.

Embodiment 28. A wound dressing according to any one of embodiments 1 to 27, wherein the wound dressing comprises a tear location located along at least one second strut, wherein the tear location is positioned between a pair of adjacent second windows, wherein the support layer forming the second strut is configured to preferentially separate at the tear location.

Embodiment 29. A wound dressing according to any one of embodiments 1 to 28, wherein the wound dressing comprises a tear location located along at least one intermediate strut, wherein the tear location is positioned between a pair of adjacent intermediate windows, wherein the support layer forming the intermediate strut is configured to preferentially separate at the tear location.

Embodiment 30. A wound dressing according to any one of embodiments 27 to 29, wherein the support layer is not attached to the backing at the tear location of any one of the first strut, the second strut, and the intermediate strut.

Embodiment 31. A wound dressing according to any one of embodiments 27 to 30, wherein a notch is formed in an edge of the support layer at the tear location of any one of the first strut, the second strut, and the intermediate strut.

Embodiment 32. A wound dressing according to any one of embodiments 27 to 30, wherein a slit is formed in an edge of the support layer at the tear location of any one of the first strut, the second strut, and the intermediate strut.

Embodiment 33. A wound dressing according to any one of embodiments 27 to 30, wherein the support layer comprises a line of weakness extending between each pair of adjacent windows at the tear location of any one of the first strut, the second strut, and the intermediate strut.

Embodiment 34. The wound dressing of any one of embodiments 1 to 33, wherein the first and second lateral edges of the backing extend substantially parallel to the longitudinal axis.

Embodiment 35. The wound dressing of any one of embodiments 1 to 34, wherein one or more of the first window, the second window, and the intermediate window comprise a maximum width measured along the longitudinal axis of 1 centimeter or more.

Embodiment 36. The wound dressing of any one of embodiments 1 to 35, wherein each window of the plurality of first windows, the plurality of second windows, and the plurality of intermediate windows comprises a maximum width measured along the longitudinal axis of 4 centimeters or less.

Embodiment 37. The wound dressing of any one of embodiments 1 to 36, wherein each window of the plurality of first windows, the plurality of second windows, and the plurality of intermediate windows comprises a maximum length measured along a lateral axis extending transverse to the longitudinal axis of 2 centimeters or more.

Embodiment 38. The wound dressing of any one of embodiments 1 to 37, wherein each pair of adjacent windows and the strut located therebetween of the plurality of first windows, the plurality of second windows, and the plurality of intermediate windows comprises a maximum window width to minimum strut width ratio of 0.25 or more, optionally 0.5 or more, optionally 1 or more, or optionally 2 or more.

Embodiment 39. The wound dressing of any one of embodiments 1 to 38, wherein each pair of adjacent windows and the strut located therebetween of the plurality of first windows, the plurality of second windows, and the plurality of intermediate windows comprises a maximum window width to minimum strut width ratio of 4 or less, optionally 3.5 or less, optionally 3 or less, or optionally 2.5 or less.

Embodiment 40. A kit comprising a sealed package containing: one or more wound dressings according to any one of embodiments 1 to 39; packing material, wherein the packing material optionally comprises open cell foam; and a port with tubing.

Embodiment 41. A method of deploying a wound dressing according to any one of embodiments 1 to 39, the method comprising: removing the release liner from the adhesive; attaching the backing over a treatment site using the adhesive; and removing the one or more of the first section of the support layer, the second section of the support layer, and the intermediate section of the support layer after attaching the backing over the treatment site.

Embodiment 42. A method according to embodiment 41, wherein the method comprises cutting the wound dressing along a longitudinal cut line extending from the first end to the second end of the wound dressing to reduce the size of the wound dressing before removing the release liner.

Embodiment 43. A method according to embodiment 42, wherein the longitudinal cut line is located in the intermediate section between the first tab junction and the second tab junction.

Embodiment 44. A method according to embodiment 42, wherein the longitudinal cut line is located in the first section or the second section of the support layer.

Embodiment 45. A method according to any one of embodiments 42 to 44, wherein the longitudinal cut line is aligned with the longitudinal axis.

Embodiment 46. A method according to any one of embodiments 41 to 45, wherein the method comprises cutting the wound dressing along a transverse cut line extending in a direction transverse to the longitudinal axis of the wound dressing to reduce the size of the wound dressing before removing the release liner.

Embodiment 47. A method according to embodiment 44, wherein the transverse cut line passes through one or both of the first tab junction and the second tab junction.

TEST METHODS

Total Hand

The flexibility or stiffness of film can be determined by measuring the amount of force required to bend the sample under test. A stiffer material will require a higher force than a material that is not as stiff. The measured value is referred to herein as "total hand" and selected materials were tested using a Model 211-10 Handle-O-Meter from Thwing Albert Instrument Company. The sample size tested in each instance was a square of 10 cm×10 cm. The slot width was 10 mm. Each test specimen was tested on each side in both the cross and machine direction of the sample. As a result, four readings per sample were obtained and the sum of these four readings is the Total Hand value for that sample.

Trouser Tear Strength

The trouser tear strength test was conducted using a Zwick/Roell Z005 tester. The sample size tested in each instance was a square of 7.5 cm×7.5 cm. For a film or paper material, a 2.5 cm long slit is cut into one edge of the machine or cross direction part of the sample such that the slit is centered along that edge. For a non-woven material with no film reinforcement, the 2.5 cm slit in the sample is made in the machine direction of the sample. If necessary for adequate gripping of the sample in the jaws of the tester, the edges are folded with the slit onto each other such that there is an approximately 0.6 cm overlap of folded material. One edge of the cut material is placed into the top jaw of the tensile tester (with the slit centered in the clamp) and the other edge of the bottom of the tensile tester. The remaining material should be on the side away from the operator. The test is then conducted at 2.5 cm/s starting from a jaw gap of 2.5 cm.

The invention may be further illustrated by the following examples, but the particular materials and amounts thereof recited in these examples, as well as other conditions and details, should not be construed to unduly limit this invention.

EXAMPLES

Example 1

A 23 micron thick polyester film coated with polyvinyl acetate to a total thickness for the coated film of 100 microns (this material is used as the top support layer on 3M™ TEGADERM™ Hydrocolloid Thin Dressing). When tested as described herein, the polyvinyl acetate coated polyester film had an average trouser tear strength of 388+/−28 grams for five test samples. The average total hand (as measured using a handle-o-meter as described herein) for five samples of this material was 83+/−6 grams for a 10 mm gap. The average ultimate elongation for five samples of this material was 120+/−20 percent.

Example 2

A 15 micron thick polyester film coated with polyvinyl acetate to a total thickness for the coated film of 50 microns (this material is used as the top support layer (with the paper tabs carefully removed) from 3M™ TEGADERM™ Drape supplied with the V.A.C.® SIMPLACE™ Dressing (Acelity, San Antonio, Tex.)). When tested as described herein, the polyvinyl acetate coated polyester film had an average trouser tear strength of 327+/−6 grams for five test samples. The average total hand (as measured using a handle-o-meter as described herein) for five samples of this material was 27+/−7 grams for a 10 mm gap. The average ultimate elongation for five samples of this material was 73+/−23 percent.

Comparative Example A

An 80# bleached calendared paper coated polyethylene C1S/Silicone C1S from Loparex, Inc. (Hammond, Wis.) was obtained and tested. When tested as described herein, the material had an average trouser tear strength of 93+/−5 grams for five test samples. The average total hand (as measured using a handle-o-meter as described herein) for five samples for this material was 1940+/−90 grams for a 10 mm gap. The average ultimate elongation for five samples of this material was 2.6+/−0.4 percent.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the scope of the invention. These and other embodiments are within the scope of the following claims.

The invention claimed is:

1. A wound dressing comprising:
an elastic film backing comprising a first major surface, a second major surface opposite the first major surface, and a perimeter that includes a first end, a second end opposite the first end, first and second lateral edges, the lateral edges extending from the first end to the second end, and a longitudinal axis extending from the first end to the second end;
adhesive disposed on the first major surface of the backing; and
a support layer attached to the second major surface of the backing, wherein the support layer comprises a first section, a second section, and an intermediate section, wherein each of the first, second, and intermediate sections extend from the first end to the second end, wherein the first section extends from the first lateral edge of the backing to a first tab junction with the intermediate section, wherein the second section extends from the second lateral edge of the backing to a second tab junction with the intermediate section;
wherein the support layer of the first tab junction comprises a first separation feature extending from the first end to the second end along the first tab junction, wherein separation of the support layer along the first separation feature forms a first section peel tab on the first section and a first intermediate tab on the intermediate section, wherein both the first section peel tab and the first intermediate tab extend from the first end to the second end of the backing;
wherein the support layer of the second tab junction comprises a second separation feature extending from the first end to the second end along the second tab junction, wherein separation of the support layer along the second separation feature forms a second section peel tab on the second section and a second intermediate tab on the intermediate section, wherein both the second section peel tab and the second intermediate tab extend from the first end to the second end of the backing;
wherein the first section of the support layer comprises a first frame that extends around a perimeter of the first section, and a plurality of first windows arranged along the longitudinal axis, wherein the second major surface of the backing is exposed within each first window of the plurality of first windows, and wherein each pair of adjacent first windows is separated from each other by a first strut;
wherein the second section of the support layer comprises a second frame that extends around a perimeter of the second section, and a plurality of second windows arranged along the longitudinal axis, wherein the second major surface of the backing is exposed within each second window of the plurality of second windows, and wherein each pair of adjacent second windows is separated from each other by a second strut;
wherein the intermediate section of the support layer comprises an intermediate frame that extends around a perimeter of the intermediate section, and a plurality of intermediate windows arranged along the longitudinal axis, wherein the second major surface of the backing is exposed within each intermediate window of the plurality of intermediate windows, and wherein each pair of adjacent intermediate windows is separated from each other by an intermediate strut.

2. A wound dressing according to claim 1, wherein at least a portion of the support layer forming the first section peel tab and the first intermediate tab is not attached to the second major surface of the backing, and wherein at least a portion of the support layer forming the second section peel tab and the second intermediate tab is not attached to the second major surface of the backing.

3. A wound dressing according to claim 1, wherein the first separation feature comprises a slit formed through the support layer, and wherein the second separation comprises a slit formed through the support layer.

4. A wound dressing according to claim 1, wherein a first handle tab is located along and extends away from the first lateral edge of the backing from the first end to the second end of the backing.

5. A wound dressing according to claim 1, wherein the first section of the support layer comprises a plurality of first slits formed through the support layer, wherein the plurality of first slits are located between the first windows and the first lateral edge of the backing.

6. A wound dressing according to claim 5, wherein the plurality of first slits are aligned along the first lateral edge of the backing.

7. A wound dressing according claim 5, wherein the plurality of first slits do not intersect the first lateral edge of the backing.

8. A wound dressing according to claim 5, wherein one or more first slits of the plurality of first slits are located between the first struts separating the first windows.

9. A wound dressing according to claim 5, wherein at least one slit of the plurality of first slits intersects a perimeter of a first window.

10. A wound dressing according to claim 1, wherein the second section of the support layer comprises a plurality of second slits formed through the support layer, wherein the plurality of second slits are located between the second windows and the second lateral edge of the backing.

11. A wound dressing according to claim 10, wherein the plurality of second slits are aligned along the second lateral edge of the backing.

12. A wound dressing according to claim 1, wherein the wound dressing comprises a tear location located along at least one first strut in the first section of the support layer, wherein the tear location is positioned between a pair of adjacent first windows, wherein the support layer forming the first strut is configured to preferentially separate at the tear location.

13. A wound dressing according to claim 1, wherein the wound dressing comprises a tear location located along at least one second strut in the second section of the support layer, wherein the tear location is positioned between a pair of adjacent second windows, wherein the support layer forming the second strut is configured to preferentially separate at the tear location.

14. A wound dressing according to claim 1, wherein the wound dressing comprises a tear location located along at least one intermediate strut in the intermediate section of the support layer, wherein the tear location is positioned between a pair of adjacent intermediate windows, wherein the support layer forming the intermediate strut is configured to preferentially separate at the tear location.

15. A wound dressing according to claim 12, wherein the support layer is not attached to the backing at the tear location of any one of the first strut, the second strut, and the intermediate strut.

16. A wound dressing according to claim 12, wherein the support layer comprises a line of weakness extending between each pair of adjacent windows at the tear location of any one of the first strut, the second strut, and the intermediate strut.

17. A kit comprising a sealed package containing:
one or more wound dressings according to 1;
packing material, wherein the packing material comprises open cell foam; and
a port with tubing.

18. A method of deploying a wound dressing according to claim 1, the method comprising:
removing the release liner from the adhesive;
attaching the backing over a treatment site using the adhesive; and
removing one or more of the first section of the support layer, the second section of the support layer, and the intermediate section of the support layer after attaching the backing over the treatment site.

* * * * *

UNITED STATES PATENT AND TRADEMARK OFFICE
CERTIFICATE OF CORRECTION

PATENT NO. : 11,033,436 B2  
APPLICATION NO. : 16/348212  
DATED : June 15, 2021  
INVENTOR(S) : David Holm et al.

Page 1 of 1

It is certified that error appears in the above-identified patent and that said Letters Patent is hereby corrected as shown below:

In the Specification

<u>Column 1</u>  
Lines 26-28     Delete ", OP-SITE (T. J. Smith & Nephew, Hull, England, and U IPLEX (Howe Medical, Largo, Fla.) and insert -- , and OP-SITE (T. J. Smith & Nephew, Hull, England --, therefor.

<u>Column 20</u>  
Line 52     Delete "2-ethylehexylacrylate" and insert -- 2-ethylhexylacrylate --, therefor.

<u>Column 21</u>  
Line 58     Delete "Germany)" and insert -- Germany). --, therefor.

<u>Column 26</u>  
Line 38 (Approx.)     Delete "Thwing Albert" and insert -- Thwing-Albert --, therefor.

In the Claims

<u>Column 29</u>  
Line 16     In Claim 7, after "according" insert -- to --.

<u>Column 30</u>  
Line 26     In Claim 17, delete "to" and insert -- to claim --, therefor.

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*